United States Patent
Chalekson

(10) Patent No.: US 10,939,906 B2
(45) Date of Patent: Mar. 9, 2021

(54) TISSUE FIXATION AND CLOSURE SUTURE ARTICLES AND SUTURE PLACEMENT DEVICES

(71) Applicant: Tack Surgical, LLC, Solana Beach, CA (US)

(72) Inventor: Charles P. Chalekson, Templeton, CA (US)

(73) Assignee: Tack Surgical, LLC, Solano Beach, CA (US)

( * ) Notice: Subject to any disclaimer, the term of this patent is extended or adjusted under 35 U.S.C. 154(b) by 401 days.

(21) Appl. No.: 15/809,795

(22) Filed: Nov. 10, 2017

(65) Prior Publication Data

US 2018/0132843 A1 May 17, 2018

Related U.S. Application Data

(60) Provisional application No. 62/420,796, filed on Nov. 11, 2016.

(51) Int. Cl.
*A61B 17/04* (2006.01)
*A61B 17/06* (2006.01)
*A61B 17/00* (2006.01)

(52) U.S. Cl.
CPC ...... *A61B 17/0487* (2013.01); *A61B 17/0401* (2013.01); *A61B 17/06166* (2013.01); *A61B 2017/00557* (2013.01); *A61B 2017/0409* (2013.01); *A61B 2017/0412* (2013.01); *A61B 2017/0417* (2013.01); *A61B 2017/0458* (2013.01); *A61B 2017/0464* (2013.01); *A61B 2017/0472* (2013.01); *A61B 2017/0488* (2013.01)

(58) Field of Classification Search
CPC ............ A61B 17/0401; A61B 17/0487; A61B 2017/0409; A61B 2017/0412; A61B 2017/0417; A61B 2017/0458; A61B 2017/0464; A61B 2017/0472; A61B 2017/0488

See application file for complete search history.

(56) References Cited

U.S. PATENT DOCUMENTS

| | | | | |
|---|---|---|---|---|
| 6,174,323 B1 * | 1/2001 | Biggs | ............... | A61B 17/00234 606/144 |
| 6,997,189 B2 * | 2/2006 | Biggs | ............... | A61B 17/00234 128/898 |
| 7,087,064 B1 * | 8/2006 | Hyde | ............... | A61B 17/00234 606/139 |
| 8,545,535 B2 | 10/2013 | Hirotsuka et al. | | |

(Continued)

*Primary Examiner* — Gregory A Anderson
(74) *Attorney, Agent, or Firm* — Ice Miller LLP

(57) ABSTRACT

The present invention includes a suture article and a suture placement device adapted to insert into opposing tissue surfaces the anchors of a suture article having anchors on its terminal ends, the device comprising in general terms: (a) an optional handle portion; (b) an insertion portion extending from the handle having a distal end comprising anchor-directing portions that diverge from one another so as to form a V-shape, adapted to releasably engage the anchors; and (c) a hollow cinching cannula/suture conduit slidingly engaged by the handle portion so as to be moveable between a position relatively nearer the handle and a position relatively nearer the insertion portion distal end.

6 Claims, 19 Drawing Sheets

(56) References Cited

U.S. PATENT DOCUMENTS

| | | | |
|---|---|---|---|
| 8,758,220 B2* | 6/2014 | Gobron | A61F 2/0045 600/37 |
| 9,393,007 B2* | 7/2016 | Darois | A61B 17/0057 |
| 9,414,921 B2* | 8/2016 | Miller | A61B 17/068 |
| 9,744,038 B2* | 8/2017 | Dahlgren | A61F 2/2445 |
| 2004/0254593 A1 | 12/2004 | Fallin et al. | |
| 2005/0177180 A1* | 8/2005 | Kaganov | A61F 2/2445 606/151 |
| 2005/0192599 A1* | 9/2005 | Demarais | A61B 17/12022 606/151 |
| 2005/0192629 A1* | 9/2005 | Saadat | A61B 17/0487 606/221 |
| 2011/0288635 A1 | 11/2011 | Miller et al. | |
| 2012/0123541 A1 | 5/2012 | Albertorio et al. | |
| 2014/0114352 A1 | 4/2014 | Allen | |
| 2014/0128914 A1* | 5/2014 | Deitch | A61B 17/0401 606/232 |
| 2014/0214079 A1* | 7/2014 | Ewers | A61B 17/0057 606/232 |
| 2014/0214152 A1* | 7/2014 | Bielefeld | A61B 17/0401 623/2.11 |

\* cited by examiner

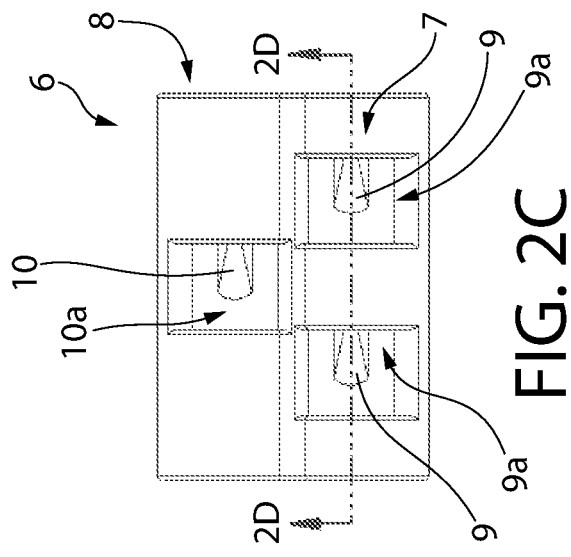
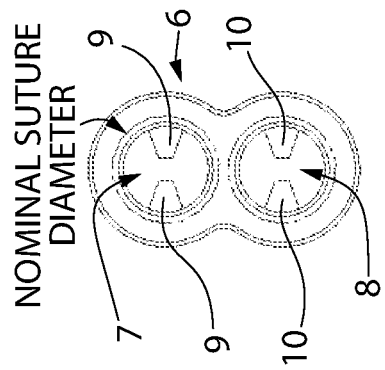
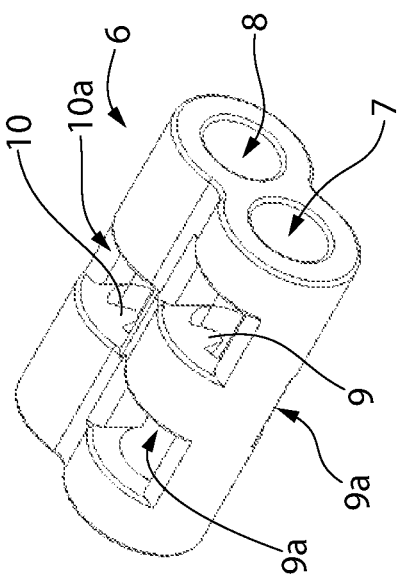
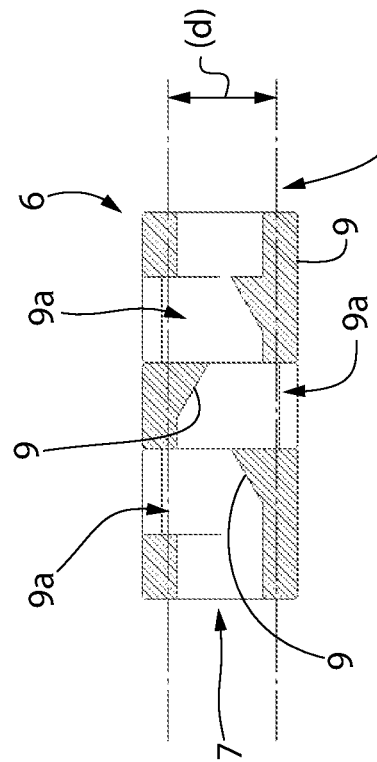

TISSUE FIXATION AND CLOSURE SUTURE ARTICLES AND SUTURE PLACEMENT DEVICES

RELATED APPLICATION DATA

This application claims the priority benefit of U.S. Provisional Application No. 62/420,796, filed Nov. 11, 2016, and incorporates by reference the disclosures of U.S. Provisional Application No. 62/443,474, filed Jan. 6, 2017, and U.S. Provisional Application No. 62/453,304, filed Feb. 1, 2017, all of which are hereby incorporated in their entirety herein by reference.

FIELD OF THE INVENTION

The present invention relates to tissue fixation and closure suture articles and suture placement devices for surgery and the like.

BACKGROUND OF THE INVENTION

Surgical procedures can result in creation of a void around tissues that normally have direct contact and adherence with other tissues. The primary medical concern with respect to dead space is that fluid, or sometimes gas, can collect within this space. A seroma is the collection of this fluid within this potential space. Seromas most often occur at a surgical site where tissue has been intentionally elevated. Friction between these elevated layers, trauma to the tissue or an inflammatory response to foreign bodies [such as implants or mesh] may result in further production of this undesirable fluid.

Seromas can cause discomfort, damage surrounding tissue, compromise normal healing, create a substrate for infection, and cause troublesome aesthetic issues.

On an emotional level, seromas can be taxing for the patient and their care providers, causing anxiety and generating heavy demand for support in the form of office visits and phone calls.

Certain procedures are particularly prone to seroma formation, and result in extra precautions to prophylactically address that risk.

One option to decrease the risk is the placement of surgical drains, which may be left in place anywhere from a few days to multiple weeks. They require significant maintenance, are painful, and are mostly, but not completely effective at draining any fluid moving into the space. Drains do not prevent the production of fluid.

One option to close and remove dead space is the placement of internal quilting sutures at the time of surgery. This entails the closure of elevated tissue planes with a large number of meticulously placed sutures to close and obliterate dead space, preventing friction and establishing contact to minimize fluid production. In this spirit, post-surgical compression garments applied to stabilize the tissue to limit edema and fluid production. In addition, the surgeon may frequently place one or more drainage tubes at the site.

Nonetheless, swelling and fluid can collect either immediately or in delayed fashion, even many weeks after surgery. This can result in additional comorbidity, medical cost and procedures for the patient, even jeopardizing the procedure success itself.

Procedures prone to seromas and for which drains are commonly used are numerous but are most frequently seen in both plastic surgery and general surgery. Surgeries that involve elevation and undermining of larger amounts of tissue tend to have higher risks toward seromas.

Some examples include breast surgeries such as lumpectomies, mastectomies, reductions, abdominoplasties, body lift procedures, hernia repairs, lymph node removal, tumor resections, and manipulation of major organs.

There are major costs and complications associated with post-surgical management of dead space and typically involve seromas, infection, and hematomas [bleeding]. Serious or long-term problems related to a seromas are regarded as infrequent but can be costly, time-consuming, and require additional surgery and treatment.

However, there remains a need for efficient and effective tissue approximation in order to best reduce seroma formation, as well as to reduce or eliminate the need for draining.

SUMMARY OF THE INVENTION

In accordance with an aspect of the invention, the present invention includes suture articles, suture placement devices for tissue approximation and the like, and methods of tissue approximation.

Suture Article: Multi-Strand Suture with a Suture Lock or Cinching Fixture

The present invention includes a multi-strand suture article with a suture lock or cinching fixture, and adapted to be inserted into opposing tissue surfaces at two respective locations and to draw the tissue surfaces toward one another, the suture article comprising: (a) at least two lengths of suture material (such as filament or thread), each length having a terminal end having a tissue anchor (i.e., barbs, t-tags, knots or balloons, or any other means of tissue attachment) adapted to resist withdrawal from the respective opposing tissue surfaces, and an opposite end, the lengths being arranged alongside one another such that the terminal ends are collateral; and (b) a cinching fixture adapted to slidingly engage the lengths so as to be able to move from the opposite ends toward the terminal ends, so as to move the anchors from a relatively more distant position to a relatively near position with respect to one another, and so as to maintain the anchors in the relatively near position.

As used herein, the term "tissue anchor" or "anchor" includes any suture component that attaches to tissue to be approximated and adapted to draw such tissue toward such approximation (i.e., such as barbs, t-tags, knots or balloons).

The cinching fixture may define a non-linear suture material path for each of the two or more sub-lengths so as to provide frictional resistance to movement of the suture material.

In another embodiment, the cinching fixture is of a relatively rigid material defining a suture material path for each of the two sub-lengths, and comprising relatively flexible frictional extensions extending into each of the suture material paths so as to provide frictional resistance to movement of the suture material.

In optional additional embodiments, the suture article additionally may comprise an additional (i.e., third, fourth, fifth, etc.) length of suture material, with the additional lengths each having a terminal end having an anchor adapted to resist withdrawal from respective opposing tissue surfaces, and with the lengths being arranged alongside one another such that the terminal ends are collateral.

Method of Tissue Approximation: Using Dual/Multiple Strand Suture with Cinching Fixture The present invention includes a method of tissue approximation of two or more opposing tissue surfaces comprising generally: (a) anchoring into opposing tissue surfaces at two or more respective locations the respective anchors of a suture article comprising: (i) two or more lengths of suture material as described herein, each length having a terminal end having a tissue anchor adapted to resist withdrawal from respective opposing tissue surfaces, and an opposite end, the lengths being arranged alongside one another such that the terminal ends are collateral; and (ii) a cinching fixture adapted to slidingly engage the lengths so as to be able to move from the opposite ends toward the terminal ends; and (b) urging the cinching fixture toward the tissue anchors so as to draw the tissue surfaces toward one another. The method of the present invention may be carried out using any of the dual- or multi-strand suture articles with a suture lock or cinching fixture as described herein. Accordingly, it will be understood that the method may be carried out using a suture article additionally comprising a third length of suture material, the third length having a terminal end having a respective third anchor adapted to resist withdrawal from a third opposing tissue surface, and an opposite end, the lengths being arranged alongside one another such that the terminal ends are collateral, and wherein step (a) includes anchoring a third opposing tissue surface at a respective third location by the third anchor, and wherein step (b) includes urging the cinching fixture toward the three tissue anchors so as to draw the three tissue surfaces toward one another. This method may be extended to the use of multi-strand suture articles including four or more anchored suture lengths.

Suture Article: Angled (e.g. V-Shaped) Suture with Cinching Fixture

Another variation embodiment of the present invention is an angled (e.g., V-shaped) suture article with a suture lock or cinching fixture, and adapted to be inserted into opposing tissue surfaces to be approximated at two or more respective locations and to draw the tissue surfaces toward one another, the suture article comprising: (a) a length of suture material comprising two or more sub-lengths gathered at a point maintained at an angle to one another so as to form an intersection, each sub-length having a terminal end having an anchor adapted to resist withdrawal from the respective tissue surfaces to which they become attached; and (b) a suture lock or cinching fixture adapted to slidingly engage the sub-lengths so as to be able to move from the intersection toward the terminal ends, so as to move the anchors from a relatively more distant position to a relatively near position with respect to one another, and so as to maintain the anchors in the relatively near position.

In one example, the suture material may comprise two sub-lengths gathered at a point and maintained at an angle to one another so as to form a V-shape at an intersection, with each sub-length having a terminal end having an anchor adapted to resist withdrawal from the respective opposing tissue surfaces. The V-shape may be maintained by providing constituent suture materials that are of sufficient thickness to hold their shape, and using molded constituent suture materials with an intersection point that maintains the sub-lengths in a position extending at an angle.

It will be appreciated that the suture material may comprise more than two sub-lengths gathered at a point and maintained at an angle to one another so as to form a multi-dentate arrangement through a multi-point intersection, which may be formed using known suture material manufacturing techniques. The sub-lengths may be gathered at an intersection point so as to present a multi-anchor suture with an intersection point, with a cinching fixture adapted to progress toward the anchors so as to bring to bear a cinching force having the effect of drawing the engaged tissue portions toward one another. The length of the individual sub-lengths may be calculated to address the prospective disposition of target tissue(s) anticipated to be presented to the user, including the type, size and the relative flexibility of the respective target tissue portions and surfaces, and the orientation of the target tissue portions in space.

This cinching fixture likewise may define a non-linear suture material path for each of the two or more sub-lengths so as to provide frictional resistance to movement of the suture material.

Alternatively, the cinching fixture may define a substantially linear suture material path for each of the two or more sub-lengths so as to provide frictional resistance to movement of the suture material. In this variant, the cinching fixture typically is of a relatively rigid material defining a suture material path for each of the two or more sub-lengths, and comprising relatively flexible frictional extensions extending into each of the suture material paths so as to provide frictional resistance to movement of the suture material. Examples of these variations are described in the drawings. In still another variation, the defined suture material path(s) may be provided for more than one of the two or more sub-lengths which in turn include flexible frictional extensions extending into each of the suture material paths, examples of which are described in the drawings.

Another feature of an embodiment of the invention is that the suture article may additionally comprise a length of suture material extending about the multi-anchored (e.g., multi-anchored, tri-barbed, etc.) suture article at the intersection so as to be able to exert a counterforce to the anchored suture lengths as the cinching fixture is slid toward the anchored ends.

Method of Tissue Approximation: Using Angled (e.g. V-Shaped) Suture with Cinching Fixture The present invention includes a method of tissue approximation of two or more opposing tissue surfaces comprising generally: (a) anchoring into the opposing tissue surfaces at two respective locations the respective anchors of a suture article comprising: (i) a length of suture material comprising at least two sub-lengths maintained at an angle to one another so as to form an intersection, each the sub-length having a terminal end having an anchor adapted to resist withdrawal from respective the opposing tissue surfaces; and (ii) a cinching fixture adapted to slidingly engage the sub-lengths so as to be able to move from the intersection toward the terminal ends, so as to move the anchors from a relatively more distant position to a relatively near position with respect to one another, and so as to maintain the anchors in the relatively near position; and (b) urging the cinching fixture toward the tissue anchors so as to draw the tissue surfaces toward one another. The method of the present invention may be carried out using any of the dual- or multi-strand suture variation of the suture article with a suture lock or cinching fixture as described herein. Accordingly, it will be understood that the method may be carried out using a suture article additionally comprising a third length of suture material, the third length having a terminal end having a respective third anchor adapted to resist withdrawal from a third opposing tissue surface, and an opposite end attached at the intersection, the anchors being collateral, and wherein step (a) includes anchoring a third opposing tissue surface at a respective third location by the third anchor, and wherein step (b) includes urging the cinching fixture toward the three tissue anchors so as to draw the three tissue surfaces toward one another. This method may be extended to the use of multi-strand suture articles including four or more anchored suture lengths each having an anchor-bearing end and an opposite end affixed as the described intersection so as to create a multi-dentate suture article.

The method likewise may be carried out using a suture article additionally comprising an additional length of suture material extending about the multi-anchored suture article at the intersection, and wherein step (b) includes maintaining tension on the additional length of suture material while urging the cinching fixture toward the tissue anchors.

Multi-Anchor Single Suture or Separate Strand Suture Placement Device—Basic Elements The suture placement device of the present invention is adapted to insert into opposing tissue surfaces the anchors of a multi-anchored suture article as described herein at two or more respective locations, and to draw the anchored tissue surfaces toward one another. The suture placement device comprises in general terms: (a) an optional handle portion; (b) an insertion portion, extending from the handle where present, having a distal end comprising anchor-directing portions that diverge from one another, adapted to releasably engage the anchors; and (c) a hollow cinching cannula/suture conduit having a distal end and slidingly engaged by the handle portion so as to be moveable between a position wherein the distal end is relatively nearer the handle and a position wherein the distal end is relatively nearer the insertion portion distal end.

The present invention also includes a suture placement device adapted to insert into opposing tissue surfaces the anchors of a multi-anchored suture article at two or more respective locations, the multi-anchored suture article comprising a length of suture material having anchors on its terminal ends and comprising two or more sub-lengths maintained at an angle to one another so as to form an intersection, the device comprising: (a) an optional handle portion having an insertion-directed end; (b) an insertion portion, extending from the insertion-directed end of the handle portion where present, and comprising a proximal end and a distal end, the distal end comprising diverging anchor-directing portions that diverge from one another, the distal ends of the anchor-directing portions being hollow; and (c) a hollow cinching cannula/suture conduit having a distal end and slidingly engaged by the handle portion so as to be moveable between a position wherein the distal end is relatively nearer the handle and a position wherein the distal end is relatively nearer the insertion portion distal end, the hollow cinching cannula/suture conduit adapted to maintain a suture material extending from the insertion portion proximal end to the insertion portion distal end.

The anchor-directing portions that diverge from one another at any angle depend upon the type and presentment of the tissue to be approached and approximated. Such variations include the divergence of the two or more anchor-directing portions at one or more acute angles to present a fork-like presentation of two or more distally extending portions. For instance, the insertion portion may feature two anchor-directing portions angled from one another at an acute angle depending upon the desired application, which acute angles typically will be in the range of from about 20 to about 45 degrees in the displayed embodiment herein.

Other variations may include those using anchor-directing portions diverging from one another within the same plane to create a T-shaped insertion portion, and those featuring a pinwheel-shaped insertion point where there are more than one anchor-directing portion. Still another variation may be one wherein the anchor-directing portions diverge from one another at an acute angle but where they are reversed so as to be directed back toward the proximal end, permitting the user first to extend the device into a space, and insert the anchors by a withdrawing motion toward the user, such as through the use of insertion portions arrayed in an obtuse angle with respect to the direction of advance, as described herein. The design and construction of such variations will be apparent from the detailed description herein and may be realized through alterations to the drawn design by simply re-configuring the insertion portion.

The anchor-directing portions optionally may comprise grooves along the interior sides of the arms of the anchor-directing portions, such as the interior sides of the arms of the angled (e.g. V-shaped) in the case of dual anchor-directing portions.

The hollow cinching cannula/suture conduit may be actuated by a control knob that extends through the handle portion.

The anchor-directing portions may be designed so as to include a proximal portion comprising opposed parallel portions and a distal portion comprising opposed divergent portions, such as those forming the angled (e.g. V-shaped) in the case of dual anchor-directing portions.

The insertion portion optionally and most conveniently may be disposed between the anchor-directing portions, whether there be two or more.

The suture placement device may be loaded with a multi-anchored suture having anchors on respective ends thereof, each distal end of the anchor-directing portion being releasably engaged to the respective anchors. Additionally, and optionally, the each sub-lengths may be fit into respective grooves of the arms of the anchor-directing portions where provided.

The multi-anchored suture article loaded in the suture placement device additionally may comprise a suture lock or cinching fixture adapted to slidingly engage the sub-lengths so as to be able to move from the intersection toward the terminal ends, so as to move the anchors from a relatively distant position to a relatively near position with respect to one another, and so as to maintain the anchors in the relatively near position, to effect the tissue approximation.

The multi-anchored suture article may additionally comprise a length of suture material extending through the hollow cinching cannula/suture conduit and about the multi-anchored suture article at the intersection of the two or more suture lengths proximally of the suture lock or cinching fixture such that a counterforce may be imparted as the suture lock or cinching fixture is urged distally toward the anchors.

Alternatively, the suture placement device may be loaded with a separate strand suture, each strand having an anchor on respective ends thereof, each distal end of the anchor-directing portion being releasably engaged to the respective anchors. As with the multi-anchor suture, each sub-length optionally may be fit into respective grooves of the arms of the anchor-directing portions where provided.

Likewise, the separate strand suture article loaded in the suture placement device additionally may comprise a suture lock or cinching fixture adapted to slidingly engage the strands so as to be able to move from the intersection toward the terminal ends, so as to move the anchors from a relatively distant position to a relatively near position with respect to one another, and so as to maintain the anchors in the relatively near position, to effect the tissue approximation. The individual suture strands extend through the hollow cinching cannula/suture conduit such that a counterforce may be imparted as the suture lock or cinching fixture is urged distally toward the anchors.

A partial list of materials frequently used in medical equipment and devices of this type (other than metals, many are available as USP Class VI) may include:
Metals:
300 Series Stainless Steel
Titanium
Nickel Titanium Alloys
Aluminum
Polymers:
Polycarbonate (PC)
Acrylonitrile butadiene styrene (ABS)
ABS/PC Copolymers
Acetyl (Delrin®, Celcon®)
Modified Acrylics
Polyether Ether Ketone (PEEK)
Polypropylene (PP)
Polyethylene (PE)
Poly Vinyl Chloride (PVC)
Polytetrafluoroethylene (PTFE)
Elastomers:
Thermoplastic Elastomers (TPE)
Thermoplastic Urethanes (TPU)
Fluoroelastomer (Viton®)
Silicone
Latex
Polyisoprene
Bio-Absorbable:
Polydioxanone (PDS)
Polyglycolic Acid PGA
Polylactic Acid (PLA)
Poly-L-lactic Acid (PLLA)

It will be appreciated that the optional handle, anchor-directing portions and the hollow cinching cannula/suture conduit may be produced from any material appropriate to the intended use whether sterile or non-sterile (i.e., for uses other than surgery or treatment, such as taxidermy or post-mortem use), and with due regard to disposability where desired. For instance, the anchor-directing portions and the hollow cinching cannula/suture conduit may be produced from metal, such as medical grade aluminum, while the handle portion may be produced from metal or plastics commonly used in medical devices, typically disposable ones.

Multi-Anchor Suture Placement Device with Loaded with Multi-Anchor Suture

The present invention also includes a multi-anchor suture placement device with loaded with multi-anchor suture, and adapted to insert into opposing tissue surfaces the anchors of a multi-anchored suture article at two respective locations, the multi-anchored suture article comprising a length of suture material having anchors on its terminal ends and comprising two sub-lengths maintained at an angle to one another so as to form an intersection, the device comprising: (a) a handle portion having an insertion-directed end; (b) an insertion portion extending from the insertion-directed end of the handle portion and comprising a proximal end and a distal end, the distal end comprising anchor-directing portions that diverge from one another so as to form a V-shape, the distal ends of the anchor-directing portions being hollow; (c) a hollow cinching cannula/suture conduit having a distal end and slidingly engaged by the handle portion so as to be moveable between a position wherein the distal end is relatively nearer the handle and a position wherein the distal end is relatively nearer the insertion portion distal end, the hollow cinching cannula/suture conduit adapted to maintain a suture material extending from the insertion portion proximal end to the insertion portion distal end, and a control knob that extends through the handle portion; (d) a multi-anchored suture article comprising a length of suture material having anchors on its terminal ends and comprising two or more sub-lengths maintained or adapted to be maintained at an angle to one another so as to form an intersection, each distal end of the anchor-directing portion being releasably engaged to the respective anchors; and (e) a cinching fixture adapted to slidingly engage the sub-lengths so as to be able to move from the intersection toward the terminal ends, so as to move the anchors from a relatively distant position to a relatively near position with respect to one another, and so as to maintain the anchors in the relatively near position, the cinching fixture greater in width than the distal end of the hollow cinching cannula/suture conduit.

Single Strand Suture Placement Device with Loaded with Separate Strand Anchored Suture The present invention also includes a suture placement device adapted to insert into opposing tissue surfaces the anchors of two (or more) anchored sutures at two (or more) respective locations, each of the anchored sutures comprising a length of suture material having anchors on its terminal ends, the device comprising: (a) an optional handle portion having an insertion-directed end; (b) an insertion portion extending from the insertion-directed end of the handle portion where present, and comprising a proximal end and a distal end, the distal end comprising anchor-directing portions that diverge from one another so as to form a V-shape, the distal ends of the anchor-directing portions being hollow; (c) a hollow cinching cannula/suture conduit having a distal end and slidingly engaged by the handle portion so as to be moveable between a position wherein the distal end is relatively nearer the handle and a position wherein the distal end is relatively nearer the insertion portion distal end, the hollow cinching cannula/suture conduit adapted to maintain a suture material extending from the insertion portion proximal end to the insertion portion distal end, and a control knob that extends through the handle portion; (d) two lengths of anchored suture having an anchor on an end thereof, each distal end of the anchor-directing portion being releasably engaged to the respective anchors; and (e) a cinching fixture adapted to slidingly engage the anchored sutures so as to be able to move toward the anchors from a relatively distant position to a relatively near position with respect to one another, and so as to maintain the anchors in the relatively near position, the cinching fixture greater in width than the distal end of the hollow cinching cannula/suture conduit.

The suture articles, suture placement devices and suture placement and tissue approximation methods of the present invention may be applied to procedures prone to seromas including various forms of plastic surgery, large tumor resections, and procedures involving repositioning of major organs. The most common types of surgery that result in seromas include breast procedures, abdominoplasty, body contouring and hernia repair. Other procedures where the present inventions may be advantageously applied include those where tissue approximation is required following the use of a trocar, such as procedures involving trocar placement through the abdomen during laparoscopic surgery. Still other procedures may be those involving tissue approximation associated with securing grafts and implants.

The tissues that may be approximated through use of the subject suture articles, suture placement devices, and suture placement and tissue approximation methods may include tissues of any type having two or more generally opposed or adjacent portions that may be advantageously drawn together to a desired position.

It will be appreciated that the present invention may be applied to other fields for the tissue approximation, adjoining and fixture, such as in veterinary medicine, or providing embalming or taxidermy services, and the like.

BRIEF DESCRIPTION OF THE FIGURES

While the specification concludes with claims particularly pointing out and distinctly claiming the present invention, it is believed that the present invention will be better understood from the following description in conjunction with the accompanying Figures, in which like reference numerals identify like elements, and wherein:

FIG. 2a is a perspective view of a suture lock or cinching fixture in accordance with aspects of the present invention.

FIG. 2b is an end elevation view of a suture lock or cinching fixture in accordance with aspects of the present invention.

FIG. 2c is a plan view of a suture lock or cinching fixture in accordance with aspects of the present invention.

FIG. 2d is a lateral sectioned view, taken along line A-A of FIG. 2c, of a suture lock or cinching fixture in accordance with aspects of the present invention.

A duplicate set of FIGS. 1-31 is included for clarity purposes as Appendix A.

DETAILED DESCRIPTION

In the following detailed description of the preferred embodiment, reference is made to the accompanying drawings that form a part hereof, and in which is shown by way of illustration, and not by way of limitation, a specific preferred embodiment in which the invention may be practiced. It is to be understood that other embodiments may be utilized and that changes may be made without departing from the spirit and scope of the present invention.

Figure 1:
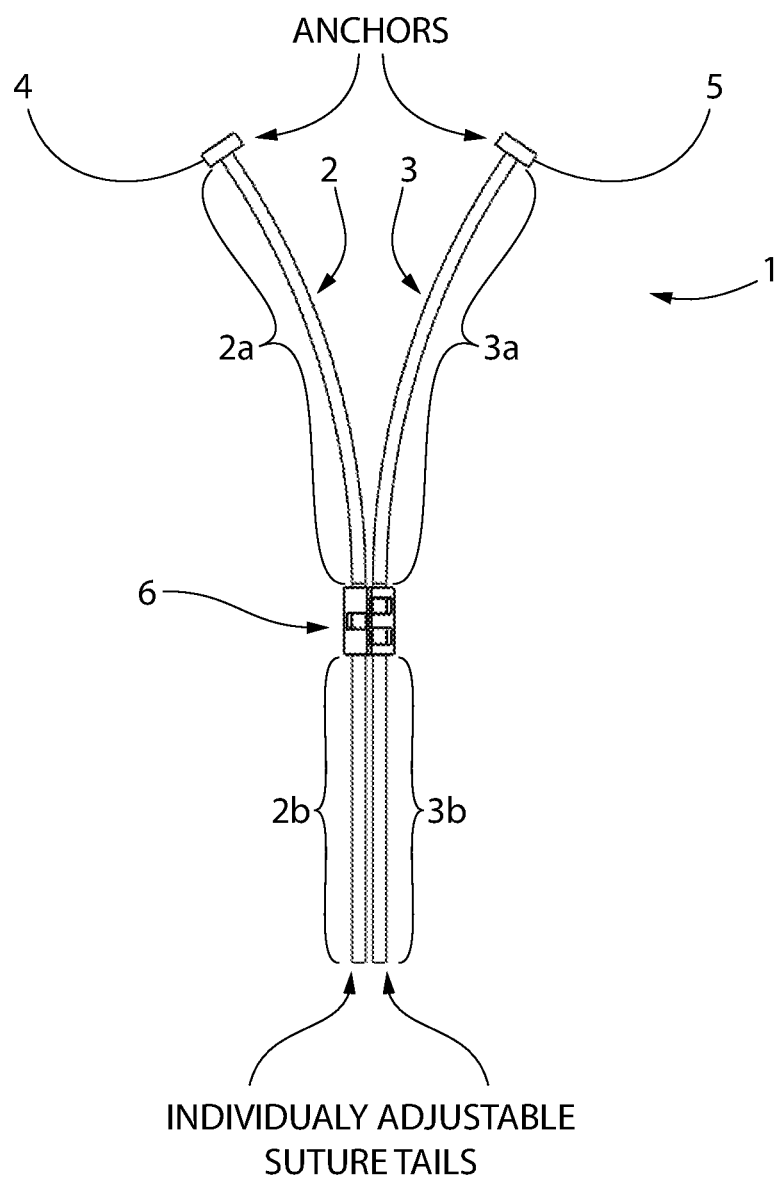
FIG. 1 is a plan view of a dual-strand suture article having barbs and a suture lock or cinching fixture in accordance with aspects of the present invention.

FIG. 1 is a plan view of a dual-strand suture article 1 having sutures 2 and 3 with respective barbs 4 and 5, and a suture lock or cinching fixture 6. The sutures 2 and 3 are independently adjustable through the suture lock or cinching fixture 6, so as to be able to take up any slack suture material between the suture lock or cinching fixture 6 and respective barbs 4 and 5. The suture article 1 is adapted to be inserted into opposing tissue surfaces at two respective locations and to draw the tissue surfaces toward one another, the suture article comprising: (a) two lengths of suture material (whether monofilament or thread) 2 and 3, each length having a terminal end (2a and 3a, respectively) having a barb 4 and 5 adapted to resist withdrawal from respective opposing tissue surfaces. The suture material lengths have an opposite end (2b and 3b, respectively), and these lengths are arranged alongside one another such that the terminal ends are collateral with respect to the cinching fixture 6. The cinching fixture 6 is adapted to slidingly engage the lengths of suture material 2 and 3 so as to be able to move from the opposite ends toward the terminal ends, so as to move the barbs 4 and 5 from a relatively more distant position to a relatively near position with respect to one another, and so as to maintain the barbs 4 and 5 in the relatively closer position to bring about and maintain the tissue approximation.

FIG. 2a is a perspective view of a suture lock or cinching fixture 6, defining suture channels 7 and 8 which define a suture material path for the suture materials 2 and 3. The suture lock or cinching fixture 6 in this variation features a series of extensions 9 opposed to respective openings 9a in channel 7 and extensions 10 opposed to respective openings 10a in channel 8 that form a non-linear path for the suture material path to bring about sufficient frictional force to resist movement from a set position, but which can be overcome by hand force as the suture lock or cinching fixture 6 is advanced toward the barbed end of the sutures.

FIG. 2b is an end elevation view of a suture lock or cinching fixture 6 also showing suture channels 7 and 8 (of a nominal suture diameter) (i.e., in a vertical arrangement) and the series of extensions 9 and extensions 10 extending into suture channels 7 and 8.

FIG. 2c is a plan view of a suture lock or cinching fixture 6 also showing suture channels 7 and 8 showing the nominal suture diameter (d), and the juxtaposition of series of extensions 9 opposed to respective openings 9a in channel 7 and extensions 10 opposed to respective openings 10a in channel 8.

FIG. 2d is a lateral sectioned view, taken along line A-A of FIG. 2c, of a suture lock or cinching fixture 6 showing suture channel 7, and showing the nominal suture diameter (d) as well as the juxtaposition of a series of extensions 9 opposed to respective openings 9a in channel 7.

Figure 3A:
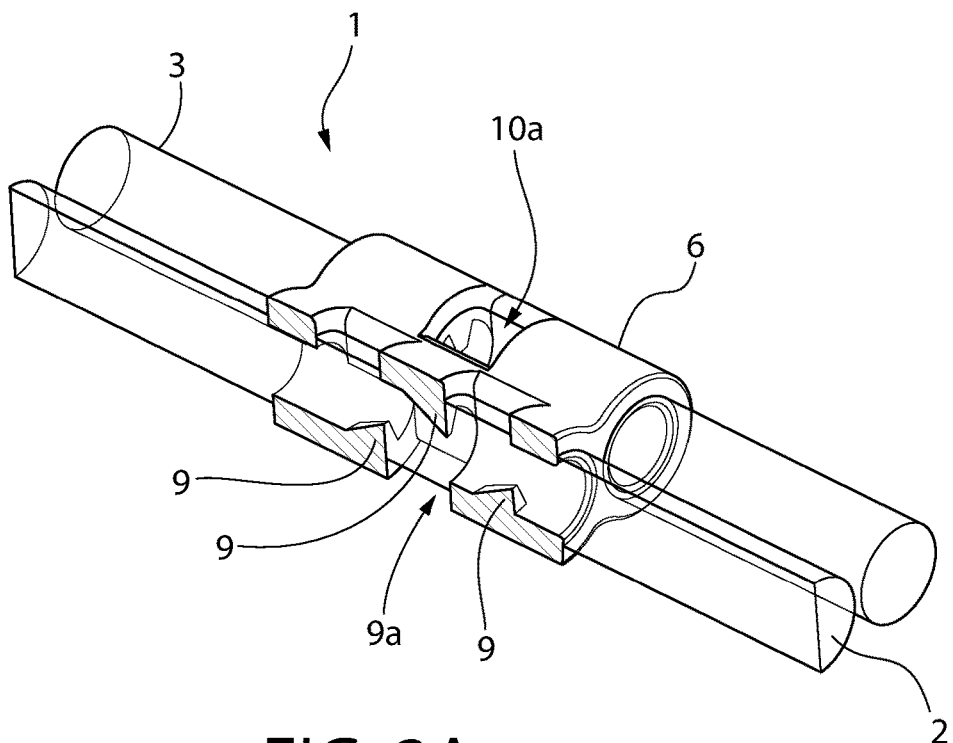
FIG. 3a is a detailed, partially sectioned perspective view of a dual-strand suture article having a suture lock or cinching fixture in accordance with aspects of the present invention.

FIG. 3a is a detailed, partially sectioned perspective view of a dual-strand suture article 1, showing the lengths of suture material 2 and 3 extending through suture channels 7 and 8 respectively (i.e., shown and described in FIG. 2a) and being held in position by suture lock or cinching fixture 6 by action of extensions 9 opposed to respective openings 9a in channel 7 and extensions 10 (see FIG. 2b) opposed to respective openings 10a in channel 8.

Figure 3B:
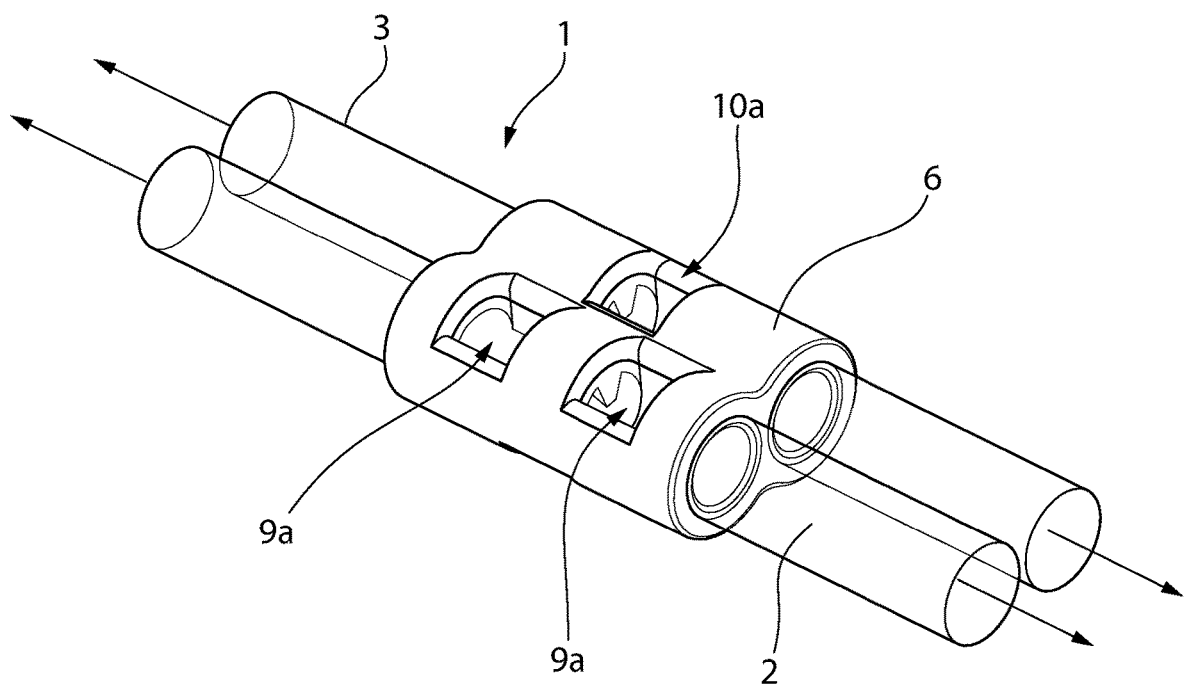
FIG. 3b is a detailed perspective view of a dual-strand suture article having a suture lock or cinching fixture in accordance with aspects of the present invention.

FIG. 3b shows a detailed perspective view of a dual-strand suture article 1 wherein like numerals refer to the aforementioned parts or aspects thereof.

As may be appreciated from FIG. 1, suture materials 2 and 3 may be combined as a single suture forming a V-shape with two sub-lengths equivalent to the lengths of suture materials 2 and 3 and joined at an intersection on the non-barbed side of the suture lock or cinching fixture 6 (i.e., by joining opposite ends 2b and 3b), and this variant may be created from any of the dual-length suture material embodiments described herein. These angled or V-shaped variants may be produced by forming the suture material of such type and thickness that the single suture holds its V-shape when at rest.

FIGS. 4a-5b show an alternative variant of the present invention that may be used in accordance with the arrangement shown in FIG. 1.

Figure 4B:
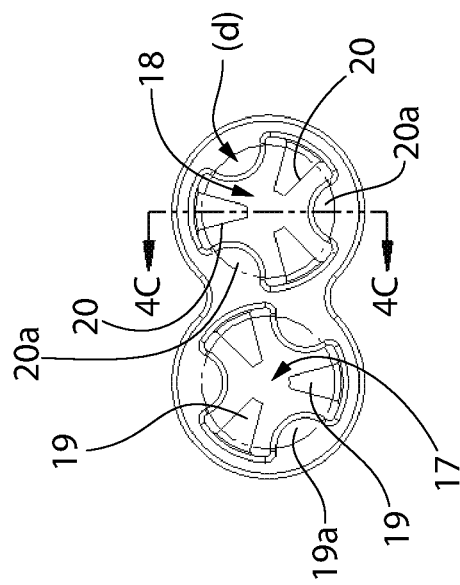
FIG. 4b is an end elevation view of a suture lock or cinching fixture in accordance with aspects of the present invention.
Figure 4C:
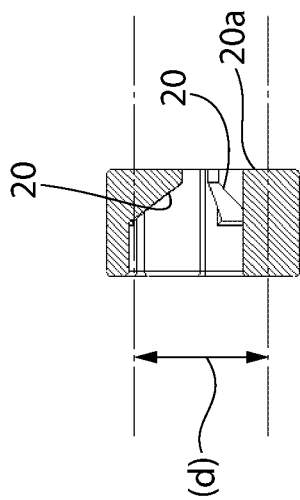
FIG. 4c is a lateral sectioned view, taken along line A-A of FIG. 4b, of a suture lock or cinching fixture in accordance with aspects of the present invention.
Figure 4A:
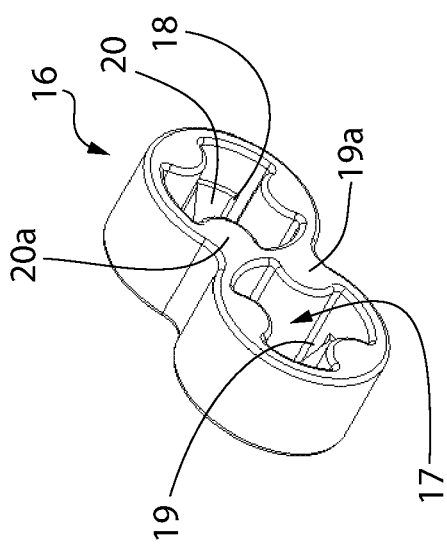
FIG. 4a is a perspective view of a suture lock or cinching fixture in accordance with aspects of the present invention.

FIG. 4a is a perspective view of a suture lock or cinching fixture 16, defining suture channels 17 and 18 which define a suture material path for the suture materials 2 and 3 (i.e., replacing suture lock or cinching fixture 6 shown in FIG. 1). The suture lock or cinching fixture 16 in this variation features a series of relatively flexible extensions 19 opposite regions of reduced diameter (i.e., less than the nominal diameter of the suture material) formed by protrusions 19a in channel 17 and relatively flexible extensions 20 opposite regions of reduced diameter formed by protrusions 20a in channel 18 that form a linear path for the suture material path. The flexible extensions and reduced diameter protrusions 19a and 20a bring about sufficient frictional force to resist movement of the suture material from a set position, but which can be overcome by hand force as the suture lock or cinching fixture 16 is advanced toward the barbed end of the sutures.

FIG. 4b is an end elevation view of a suture lock or cinching fixture 16 also showing suture channels 17 and 18 (of a nominal suture diameter (d)) (i.e., in a horizontal arrangement) and the series of relatively flexible extensions 19 and protrusions 19a, and relatively flexible extensions 20 and protrusions 20a, extending respectively into suture channels 17 and 18.

FIG. 4c is a lateral sectioned view, taken along line A-A of FIG. 4b, of the suture lock or cinching fixture 16, and showing the relative position of relatively flexible extensions 20 and protrusions 20a.

Figure 5A:
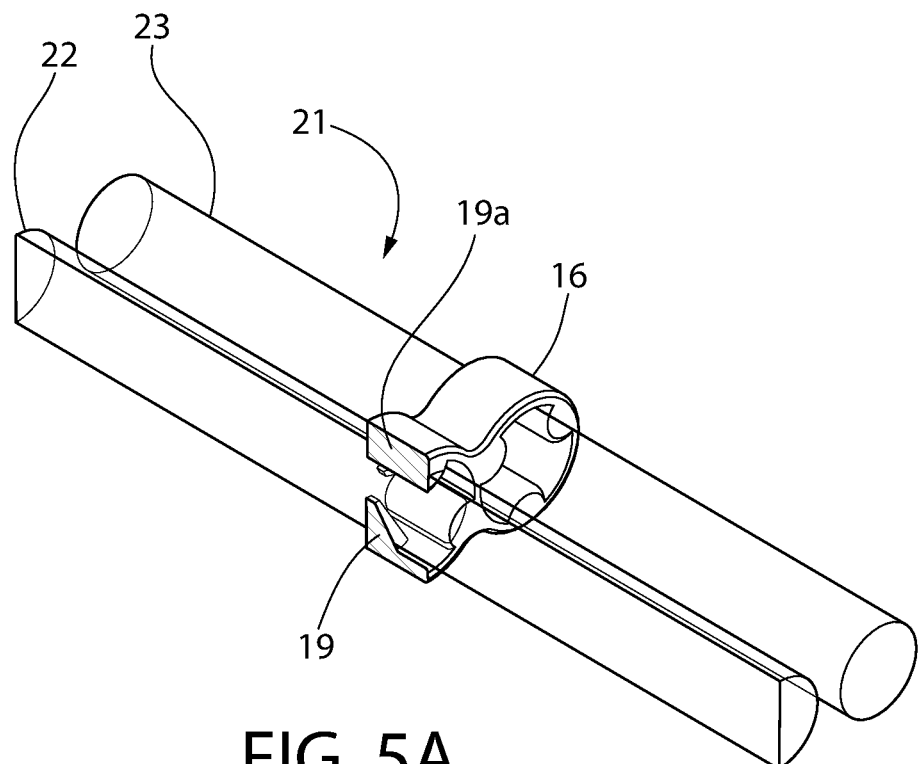
FIG. 5a is a detailed, partially sectioned perspective view of a dual-strand suture article having a suture lock or cinching fixture in accordance with aspects of the present invention.

FIG. 5a is a detailed, partially sectioned perspective view of a dual-strand suture article 21, showing the lengths of suture material 22 and 23 extending through suture channels 17 and 18 respectively (see FIG. 4a), and being held in position by suture lock or cinching fixture 16 respectively by action of relatively flexible extensions 19 and protrusions 19a, and relatively flexible extensions 20 and protrusions 20a.

Figure 5B:
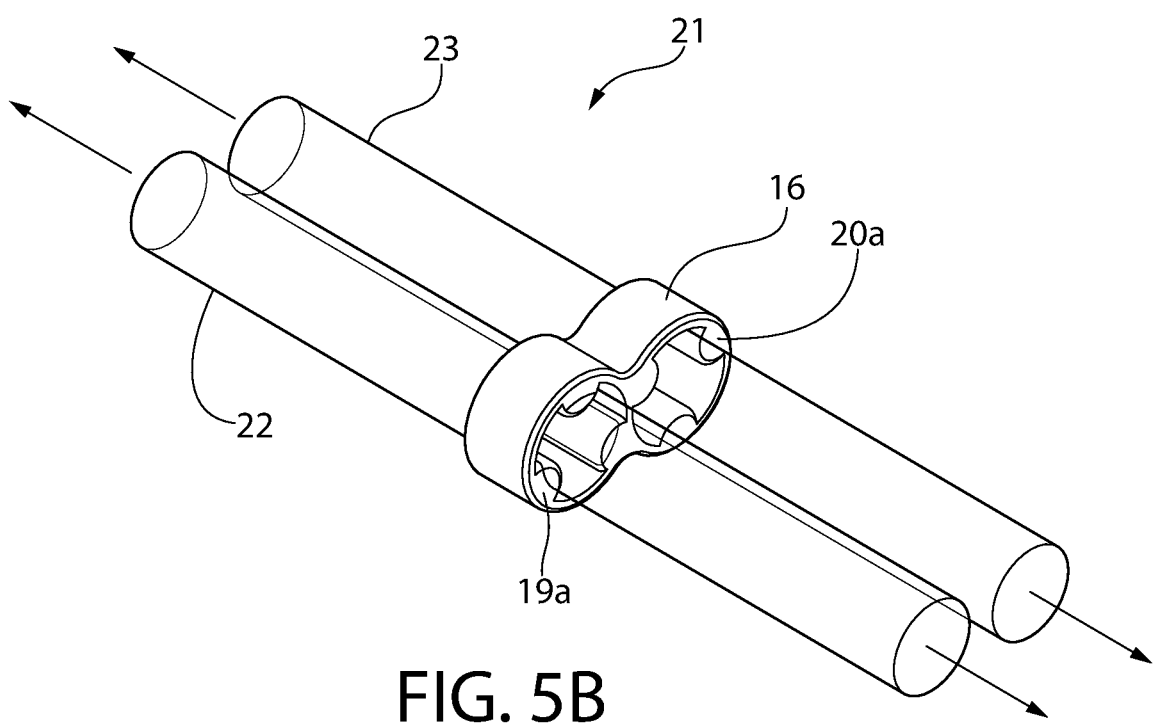
FIG. 5b is a detailed perspective view of a dual-strand suture article having a suture lock or cinching fixture in accordance with aspects of the present invention.

FIG. 5b shows a detailed perspective view of a dual-strand suture article 21 wherein like numerals refer to the aforementioned parts or aspects thereof.

FIGS. 6a-7b show an alternative variant of the present invention that may be used in accordance with the arrangement shown in FIG. 1.

Figure 6A:
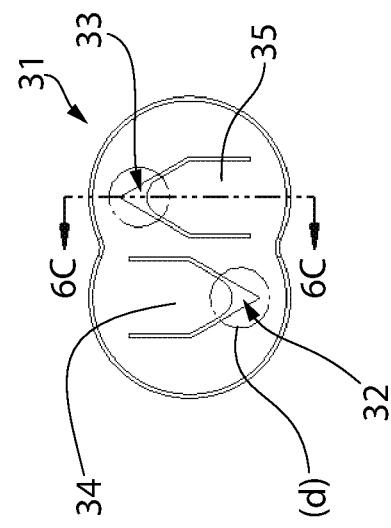
FIG. 6a is a perspective view of a suture lock or cinching fixture in accordance with aspects of the present invention.

FIG. 6a is a perspective view of a suture lock or cinching fixture 31, defining suture channels 32 and 33 which define a suture material path for the suture materials 37 and 38 (see FIGS. 7a and 7b) (i.e., replacing suture lock or cinching fixture 6 shown in FIG. 1). The suture lock or cinching fixture 31 in this variation features single relatively flexible extensions 34 and 35 respectively extending into suture channels 32 and 33 so as to form a reduced diameter suture material path. The relatively flexible extensions 34 and 35 bring to bear sufficient frictional force to resist movement of the suture material from a set position, but which can be overcome by hand force as the suture lock or cinching fixture 31 is advanced toward the barbed end of the sutures.

Figure 6B:
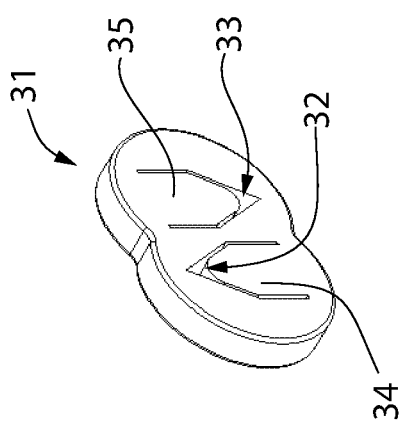
FIG. 6b is an end elevation view of a suture lock or cinching fixture in accordance with aspects of the present invention.

FIG. 6b shows an elevation view of a suture lock or cinching fixture 31 wherein like numerals refer to the aforementioned parts or aspects thereof. FIG. 6b also shows the nominal suture diameter (d).

Figure 6C:
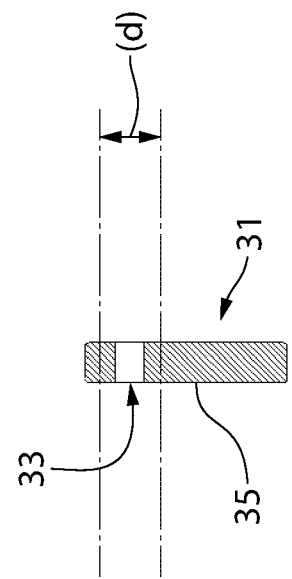
FIG. 6c is a lateral sectioned view, taken along line A-A of FIG. 6b, of a suture lock or cinching fixture in accordance with aspects of the present invention.

FIG. 6c is a lateral sectioned view of a suture lock or cinching fixture 31, taken along line A-A of FIG. 6b, wherein like numerals refer to the aforementioned parts or aspects thereof. FIG. 6c also shows the relative size of the nominal suture diameter (d), it being understood that the nominal suture diameter, opening size and extension flexibility may be varied to adjust performance of the suture lock or cinching fixture in terms of the amount of hand force needed to overcome the imposed friction, strength of locking force, etc.

Figure 7A:
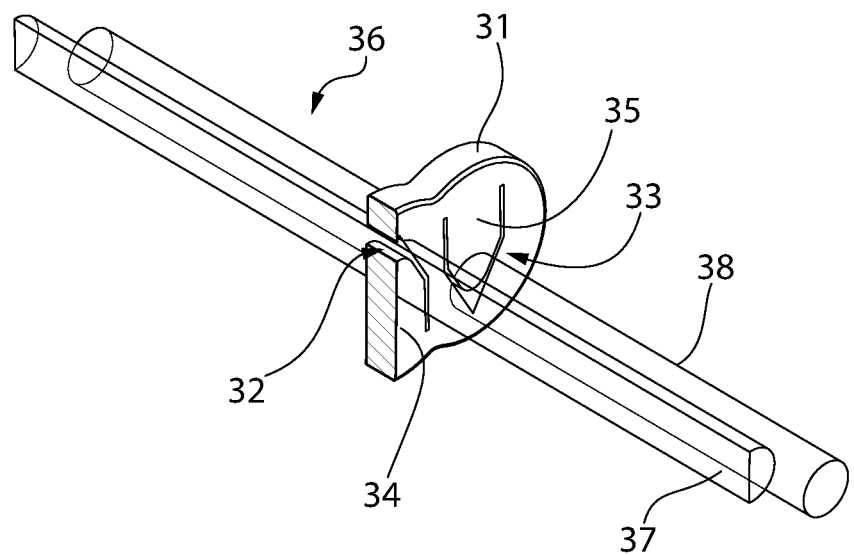
FIG. 7a is a detailed, partially sectioned perspective view of a dual-strand suture article having a suture lock or cinching fixture in accordance with aspects of the present invention.

FIG. 7a is a detailed, partially sectioned perspective view of a dual-strand suture article 36, showing the lengths of suture material 37 and 38 extending through suture channels 32 and 33 respectively, and being held in position by suture lock or cinching fixture 31 respectively by action of relatively flexible extensions 34 and 35.

Figure 7B:
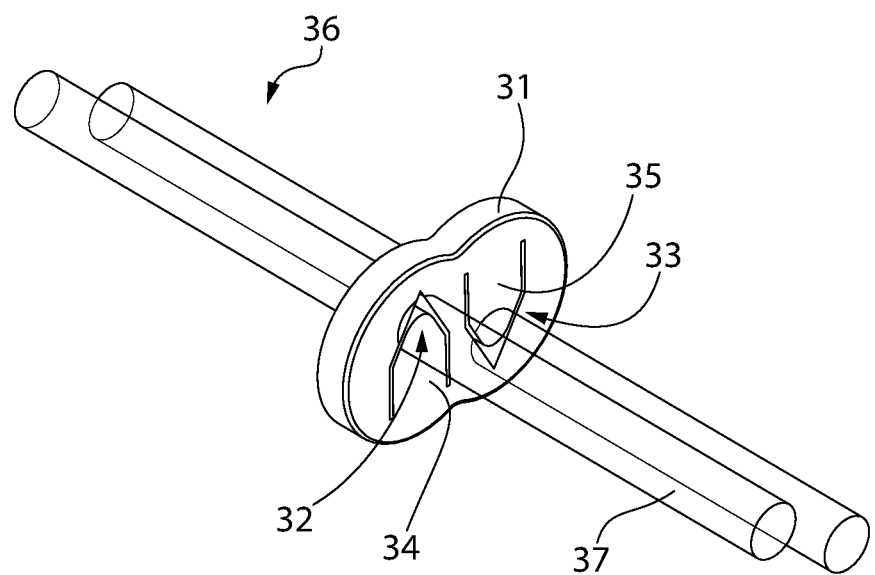
FIG. 7b is a detailed perspective view of a dual-strand suture article having a suture lock or cinching fixture in accordance with aspects of the present invention.

FIG. 7b shows a detailed perspective view of a dual-strand suture article 36 wherein like numerals refer to the aforementioned parts or aspects thereof.

FIGS. 8-10b shows several additional suture article and suture lock or cinching fixture variants that may be applied in the dual-strand, angled or V-shaped suture articles of the present invention.

Figure 8:
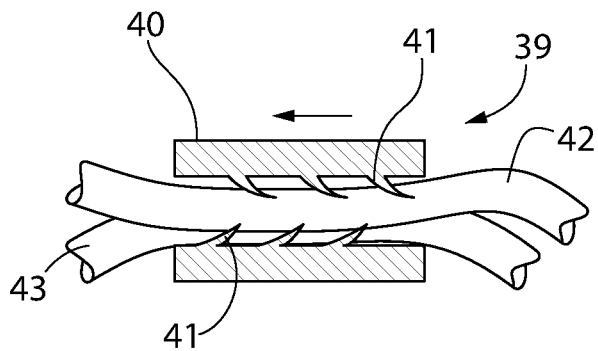
FIG. 8 is a detailed, partially sectioned perspective view of a dual-strand suture article having a suture lock or cinching fixture in accordance with aspects of the present invention

FIG. 8 is a detailed, partially sectioned perspective view of a dual-strand suture article 39 having a suture lock or cinching fixture 40 that captures both suture materials 42 and 43 in a single channel (i.e., replacing suture lock or cinching fixture 6 shown in FIG. 1). This variant features internal barbs 41 extending into the channel so as to provide a one-way zip-lock to the suture materials 42 and 43, as the suture lock or cinching fixture 40 is advanced toward the barbed ends of the sutures.

Figure 9A:
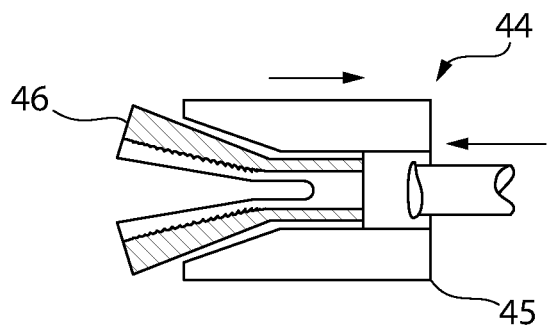
FIGS. 9a and 9b are detailed, partially sectioned perspective views of a locking progression of a dual-strand suture article having a suture lock or cinching fixture in accordance with aspects of the present invention.
Figure 9B:
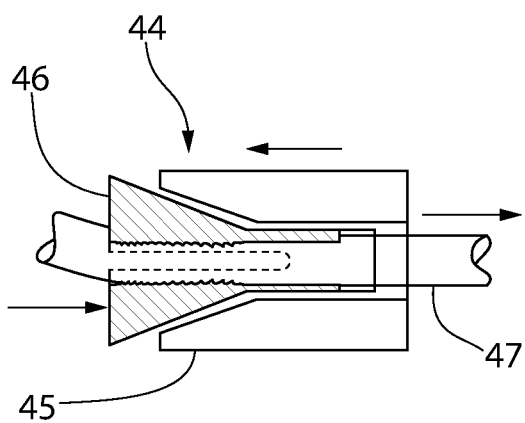

FIGS. 9a and 9b are detailed, partially sectioned perspective views of a locking progression of a single-strand suture article/cinching feature combination 44 having a suture lock or cinching fixture 45 including a collet 46 that features a toothed, barbed or otherwise gripping internal surface, and is shaped so as to be able to grip the suture material and then be drawn into the suture channel so as to provide an interference lock against the suture material 47, as shown in the progression from FIGS. 9a to 9b. This allows suture material 47 to be drawn though the suture lock or cinching fixture 45 as shown in FIG. 9a and then to be engaged by collet 46 when withdrawn in the opposite direction as shown FIG. 9b such that the collet 46 and the inner channel surface of suture lock or cinching fixture 45 cooperate to lock the suture material in place. This variant may be adapted to a dual-strand variant by forming two side-by-side suture lock or cinching fixtures 45 to provide for the cinching and locking of two individual suture strands.

Figure 10A:
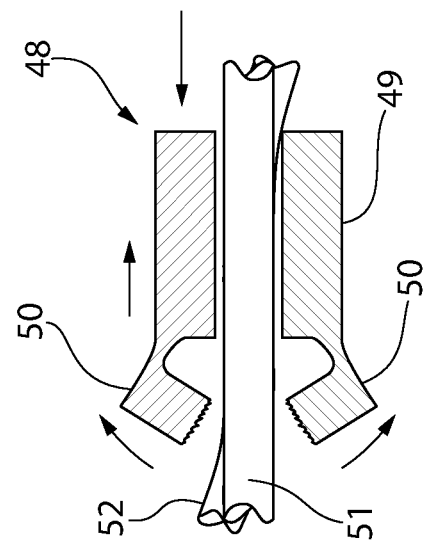
FIGS. 10a and 10b are detailed, partially sectioned perspective views of a locking progression of a dual-strand suture article having a suture lock or cinching fixture in accordance with aspects of the present invention.
Figure 10B:
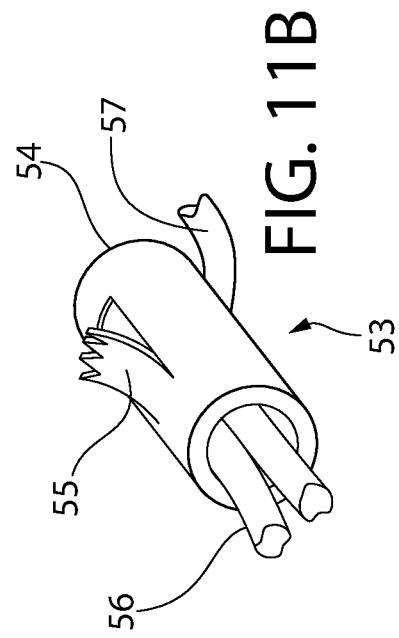

FIGS. 10a and 10b are detailed, partially sectioned perspective views of a locking progression of a dual-strand suture article 48 comprising two suture material strands 51 and 52, and a suture lock or cinching fixture 49 having a flexible, toothed (or otherwise gripping) opposed claw portions 50 that feature a toothed, barbed or otherwise gripping internal surface, the opposed claw portions 50 being shaped so as to be able to grip the suture material and be drawn into the suture channel so as to provide an interference lock against the suture material strands 51 and 52, as shown in the progression from FIGS. 10b to 10a. This allows suture material strands 51 and 52 to be drawn though the suture lock or cinching fixture 49 as shown in FIG. 10b and then to be engaged by opposed claw portions 50 when withdrawn in the opposite direction as shown FIG. 10a such that the opposed claw portions 50 cooperate to lock the suture material strands 51 and 52 in place.

Figure 11A:
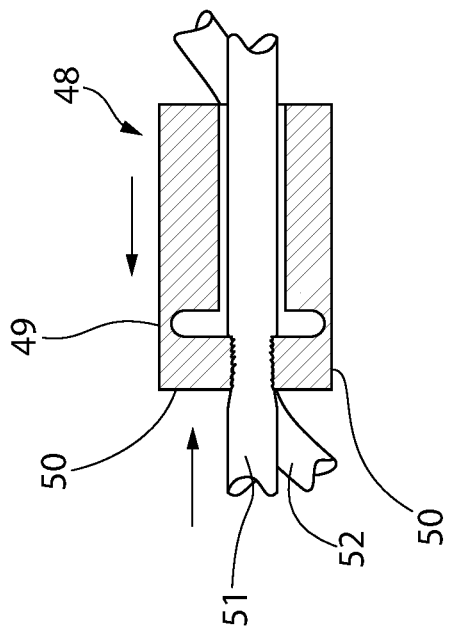
FIG. 11a is a detailed, partially sectioned perspective view of a dual-strand suture article having a suture lock or cinching fixture in accordance with aspects of the present invention.
Figure 11B:
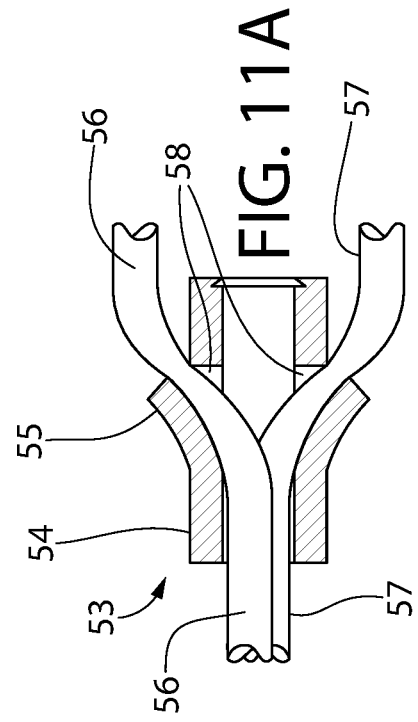
FIG. 11b is a detailed perspective view of a dual-strand suture article having a suture lock or cinching fixture in accordance with aspects of the present invention.

FIG. 11a is a detailed, partially sectioned perspective view of a dual-strand suture article 53 comprising two suture material strands 56 and 57, and a suture lock or cinching fixture 54 having a flexible, toothed (or otherwise gripping) claw portions 50 that feature a toothed, barbed or otherwise gripping internal surface, which portions govern lateral channels 58, the opposed claw portions 50 being shaped so as to be able to grip the suture material and be drawn through the lateral suture channels 58 so as to provide an interference lock against the suture material strands 56 and 57, as shown in the progression from FIGS. 11b to 11a. This allows suture material strands 56 and 57 to be drawn though the suture lock or cinching fixture 54 as shown in FIG. 11a and then to be engaged by opposed claw portions 55 when withdrawn in the opposite direction as shown FIG. 11b such that the opposed claw portions 55 cooperate to lock the suture material strands 56 and 57 in place.

It will be appreciated that the suture lock or cinching fixture may be produced in variations adapted to accommodate more than two strands of suture material by forming multiple side-by-side suture lock or cinching fixtures of the type described herein (such as suture lock or cinching fixtures comprising 3, 4 or 5+ individual suture material lengths), and this may be done through the same molding processes by which the above-described variants may be produced. Such variants permit the independent tensioning and/or cinching or locking of two or more lengths of suture material. This permits the user to independently tension each suture length and thereby bring to bear differing amounts of approximating force to each tissue attached thereto.

The suture lock or cinching fixture may be produced from known polymeric materials such as known bioresorbable polymers known and used in the art. The most common bioresorbable polymer is polylactic acid (PLA), also known as polylactide, and is made from a lactide monomer. Generally speaking, PLA is the main building block for bioresorbable polymer materials. Common derivatives of PLA are poly-L-lactide (PLLA), poly-D-lactide (PDLA) and poly-DL-lactide (PDLLA). When in the body, PLA degrades into lactic acid, a non-toxic chemical which occurs naturally in the body. Polyglycolic acid (PGA), or polyglycolide (PG), is another type of bioresorbable polymer usually used for bioresorbable sutures. The material may be copolymerised with lactic acid to form poly(lactic-co-glycolic acid), or PLGA, with e-caprolactone to form poly(glycolide-co-caprolactone), or PGCL, and with trimethylene carbonate to form poly(glycolide-co-trimethylene carbonate), or (PGA-co-TMC). PGA degrades to form glycolic acid.

The sutures that may be used in accordance with the present invention may have conventional monofilament or multifilament constructions. Examples of absorbable suture materials include absorbable polyester polymers and copolymers such as lactides, glycolides, polydioxanone, epsilon-caprolactone, polylactic acid, polyglycolic acid, and copolymers and blends thereof and equivalents thereof and the like, and may include conventional materials such as cat gut. Examples of nonabsorbable polymers include polyesters, silk, polyolefins such as polypropylene and polyethylene, nylon, and the like. Commercially available sutures that may be used with the stay suture devices of the present invention include the following sutures manufactured and sold by Ethicon, Inc., Somerville, N.J. 08876, USA such as Coated VICRYL Plus Suture, Coated VICRYL Suture, MONOCRYL Plus Suture, MONOCRYL Suture, PDS Plus Suture, PDS Suture, Surgical Gut Suture—Chromic, Surgical Gut Suture—Plain, PRONOVA Suture, ETHIBOND EXCEL Suture, ETHILON Suture, MERSILENE Suture, NUROLON Suture, PERMA-HAND Silk Suture, PROLENE Suture, and the like. The sutures will have a size that is effective to secure the tissue to be approximated in place, and the selection will be within the discretion of the surgeon. Although any size sutures may be used, typically the size of the sutures will range from a size of 2 to 6-0.

Figure 12:
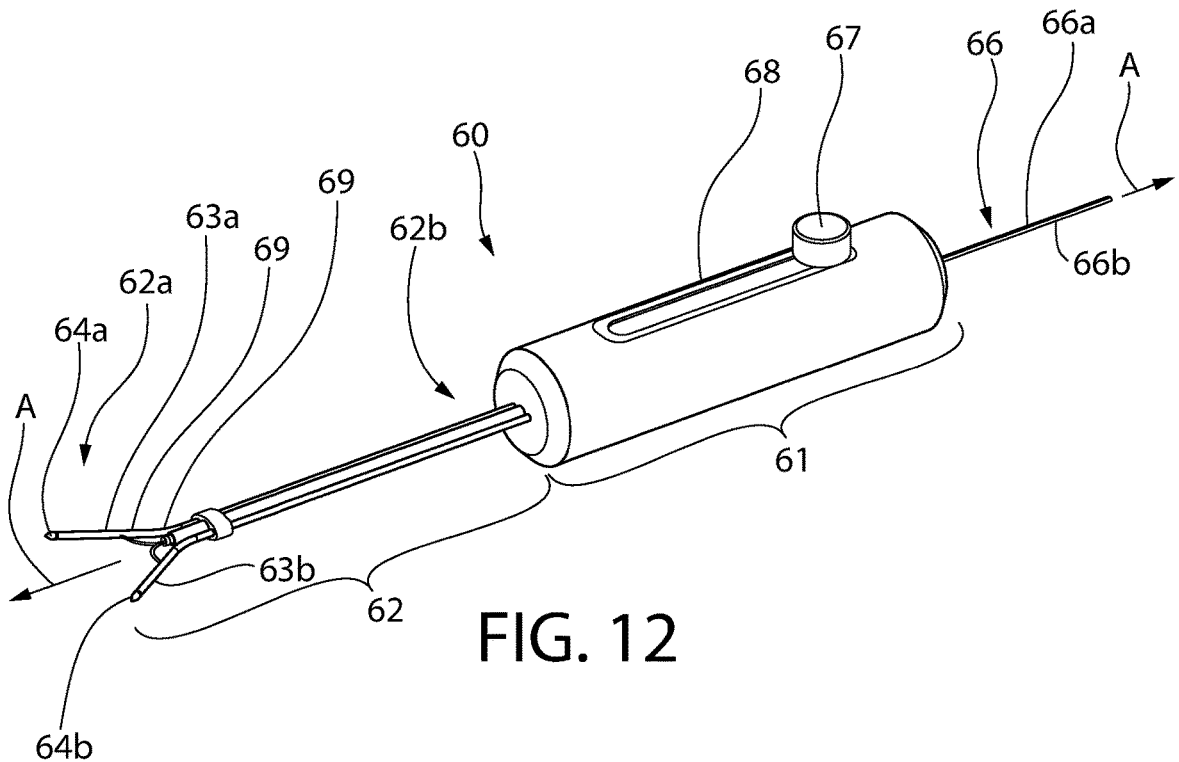
FIG. 12 is a perspective view of a suture placement device in accordance with one embodiment of the present invention.

FIG. 12 is a perspective view of a suture placement device 60 in accordance with one embodiment of the present invention. The suture placement device 60 comprises a handle portion 61 having an insertion-directed end, an insertion portion 62 extending from the insertion-directed end of the handle portion 61 and comprising a proximal end 62b and a distal end 62a, the distal end 62a comprising barb-directing portions 63a and 63b that diverge from one another so as to form a V-shape, the distal ends of the barb-directing portions being hollow to releasably hold barbs 64, as can be appreciated more clearly in FIGS. 14 and 15. This embodiment of the suture placement device features two angled "needles" that support two barb-tipped sutures (whether single suture or independent lengths). The two barb-tipped sutures where comprising independent lengths (such as 66a and 66b) are fed down the hollow cinching cannula/suture conduit 65 (see FIG. 13) that extends through a channel in the handle portion 61 and is slidingly engaged therein.

Figure 13:
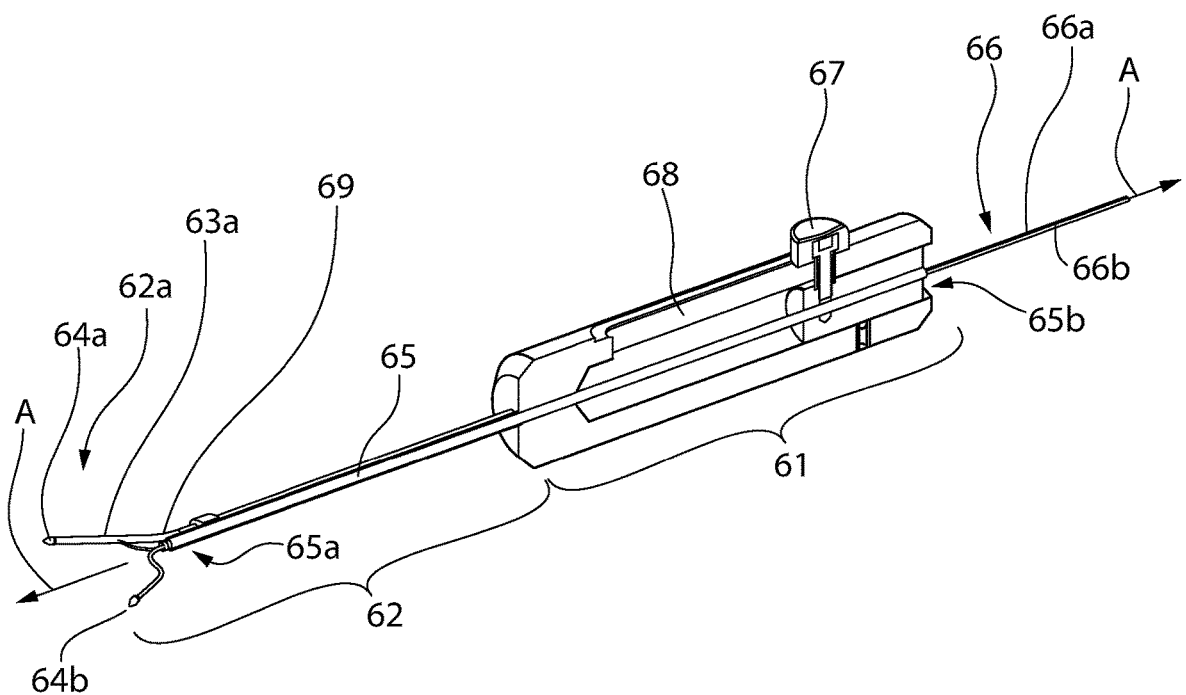
FIG. 13 is a partially sectioned perspective view of a suture placement device in accordance with one embodiment of the present invention.

FIG. 13 is a partially sectioned perspective view of a suture placement device 60 in accordance with one embodiment of the present invention. This Figure shows the hollow cinching cannula/suture conduit 65 having a distal end 65a and slidingly engaged by the handle portion 61 so as to be moveable between positions wherein the distal end 65a is relatively nearer the handle 61 and wherein the distal end 65a is relatively nearer the insertion portion's distal end 62a. The hollow cinching cannula/suture conduit 65 is slidingly contained within outer cannula 69, and is adapted to maintain a suture material 66 (i.e., comprising respective lengths 66a and 66b) extending from the insertion portion proximal end 65b to the insertion portion distal end 65a, and a control knob 67 that extends through the handle portion 61. The control knob in this embodiment may be guided in its movement by control slot 68.

FIGS. 12 and 13 thus show the suture placement device 60 featuring two angled barbed ends, the angle of the barbed ends may be at any angle, acute or obtuse, depending upon the desired application, though acute angles typically will be in the range of from about 20 to about 45 degrees in the displayed embodiment.

The suture material 66 may be in the form of a dual-strand suture (as shown in the Figures or an angled (e.g., V-shaped) suture in which case the angled (e.g., V-shaped) suture is deployed by the device with the aid of a secondary suture that is looped through the angled suture intersection (and proximally of the suture lock or cinching fixture). The angled suture provides a multi-anchored suture article comprising a length of suture material having barbs on its terminal ends and comprising two sub-lengths maintained at an angle to one another so as to form an intersection, each distal end of the anchor-directing portion being releasably engaged to respective anchors, in this case barbs at the terminal ends of suture material.

Figure 14:
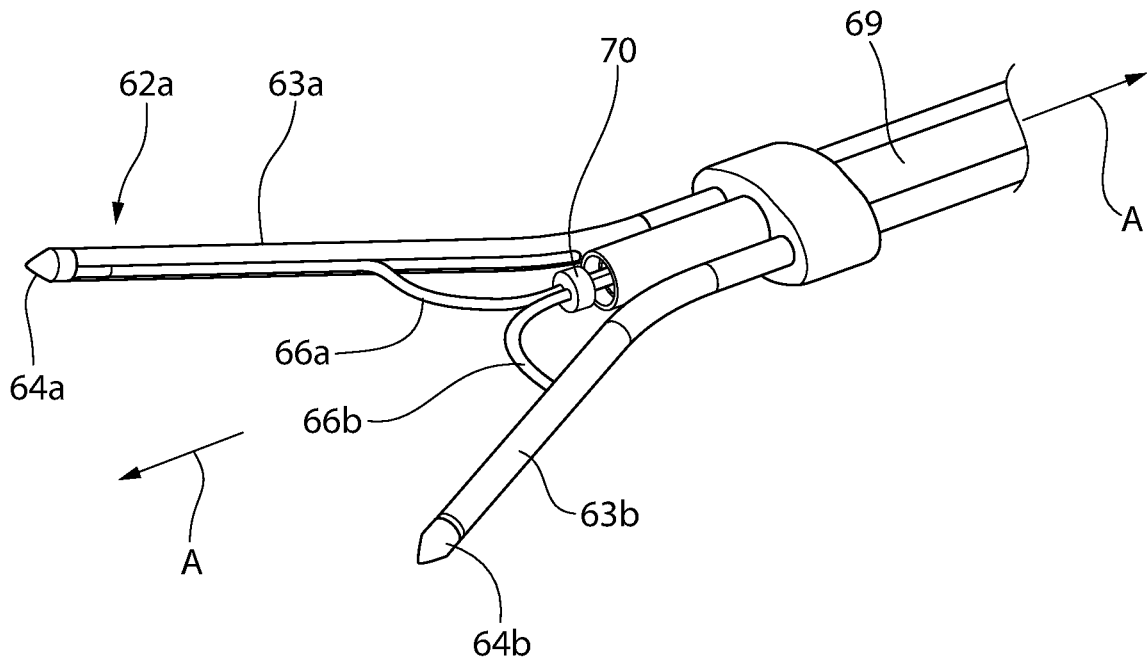
FIG. 14 is a detailed perspective view of the insertion portion of a suture placement device in accordance with one embodiment of the present invention.
Figure 15:
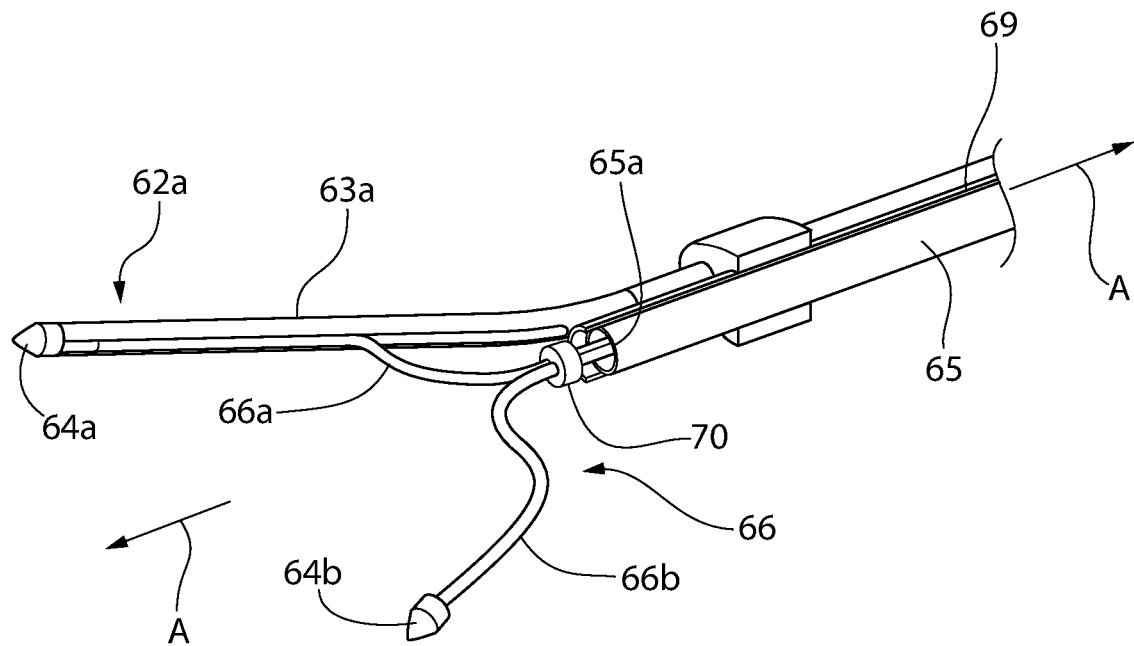
FIG. 15 is a detailed, partially sectioned perspective view of the insertion portion of a suture placement device in accordance with one embodiment of the present invention.

FIGS. 14 and 15 show suture placement device 60 in the loaded condition holding barb-tipped sutures having respective barbs 64a and 64b.

FIG. 14 is a detailed perspective view of the insertion portion 62a of a suture placement device 60 and FIG. 15 is a detailed, partially sectioned perspective view thereof. FIGS. 14 and 15 show a suture lock or cinching fixture 70 which may be any of those shown and described herein (e.g., such as suture lock or cinching fixture 6, 16, 31, 39, 44, 48 and 53). The FIGS. 14 and 15 show in greater detail how the suture lock or cinching fixture 70 is adapted to slidingly engage the suture lengths 66a and 66b and to be moved distally so as to shorten the portions of suture lengths 66a and 66b between the suture lock or cinching fixture 70 and the respective barbs 64a and 64b, once the barbs 64a and 64b have been placed in the tissue for approximation. As may be appreciated from FIGS. 14 and 15, the suture placement device 60 is loaded with the barb-tipped sutures 66a and 66b (the distal portions thereof optionally seated in respective slots in angled barb-directing portions 63a and 63b). Barbs 64a and 64b are releasably engaged respectively with barb-directing portions 63a and 63b such that the barbs may be urged into place in the tissue to be approximated, and released upon withdrawal of the device, as described in the later Figures herein.

The suture lock or cinching fixture 70 is urged distally by the hollow cinching cannula/suture conduit 65 by being slidingly engaged by the handle portion 61 (and its outer cannula 69) so as to be moveable along axis A between a position wherein the hollow cinching cannula/suture conduit distal end 65a is relatively nearer the handle 61, and a position wherein the hollow cinching cannula/suture conduit distal end 65a is relatively nearer the insertion portion distal end 62a, the hollow cinching cannula/suture conduit 65 adapted to maintain a suture material extending from the insertion portion proximal end 65b to the insertion portion distal end (i.e., opposite 65a). The inner diameter of the hollow cinching cannula/suture conduit 65 will be sized so as to be adapted to releasably capture the suture lock or cinching fixture 70 and urge distally to be able to cinch the suture portions and thereby approximate the tissue pieced by the barbs 64a and 64b.

FIGS. 14 and 15 also show that barb-directing portions 63a and 63b may be hollow on their distal ends to accept barbs 64a and 64b to be releasably engaged respectively thereby and a portion of barb-directing portions 63a and 63b may further be grooved proximally to accommodate respectively the distal ends of suture lengths 66a and 66b.

In similar fashion, where an angled, V-shaped dual barbed suture is used (i.e. where, instead of using two suture lengths 66a and 66b, these lengths are combined as an angled single suture by forming an intersection on the non-barbed (i.e., proximal) side of the suture lock or cinching fixture 70, forming sub-lengths of an angled (or V-shaped) single suture and bearing the suture lock or cinching fixture 70), an additional suture material may be threaded through the loop formed at the intersection to permit the additional suture material to provide a counterforce as the suture lock or cinching fixture 70 is urged forward (i.e., the two ends thereof extending in the same fashion as the proximal ends of suture lengths 66a and 66b extend from the hollow cinching cannula/suture conduit 65 in FIGS. 12 and 13), so as to be able to move the suture lock or cinching fixture 70 from the intersection toward the barbs 64a and 64b, so as to move barbs 64a and 64b from a relatively distant position to a relatively near position with respect to one another, and so as to maintain the barbs in the relatively closer position to effect tissue approximation.

At least a portion of the suture lock or cinching fixture 70 typically will be greater in width than the distal end 65a of the hollow cinching cannula/suture conduit 65 (such as containing a taper or the like), so as to be able to transmit urging force.

FIGS. 16-28 show a stepwise progression of the use of the suture placement device 60, and represent an example of the method of tissue approximation brought about by its use.

Figure 16:
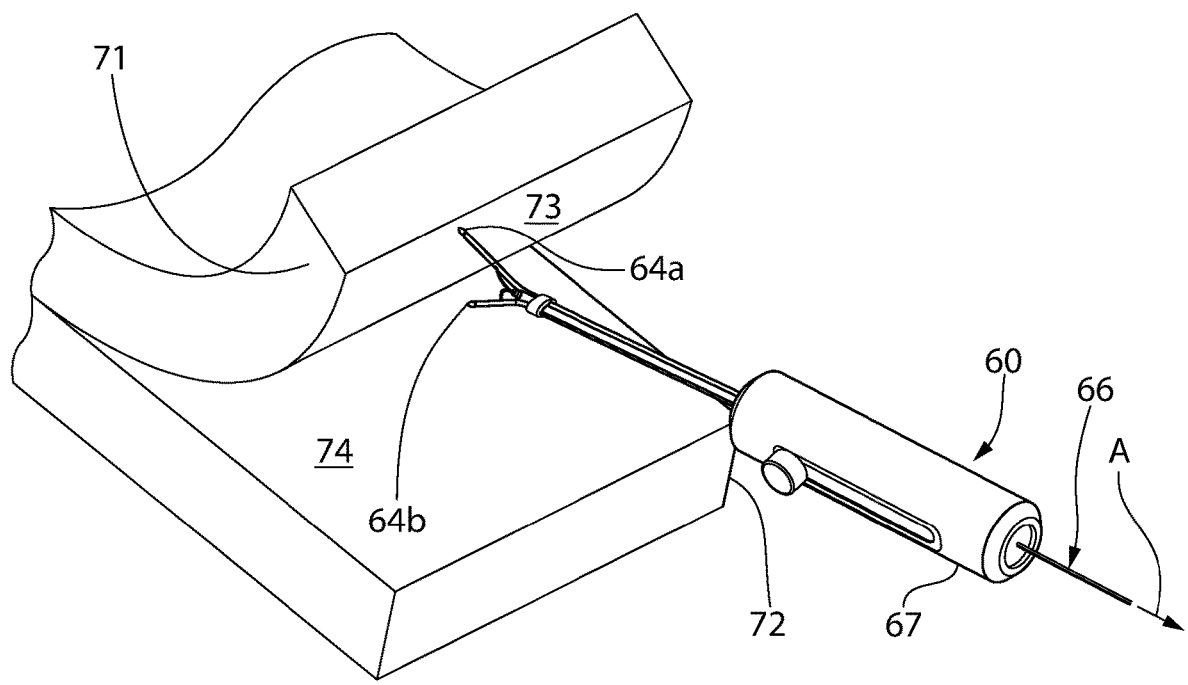
FIG. 16 is an isometric perspective view of the suture placement device in accordance with one embodiment of the present invention, shown in an approach to a representation of tissue to be joined.

FIG. 16 is an isometric perspective view of the suture placement device 60, shown in an approach to a representation of tissue to be joined, i.e., upper and lower tissue portions 71 and 72 having respective opposing surfaces 73 and 74. FIG. 16 shows the suture placement device 60 having barb-directing portions 63a and 63b being loaded with the barbs 64a and 64b as shown and described in FIGS. 12-14, and with the hollow cinching cannula/suture conduit 65 (see FIG. 17) retracted to the rear position as indicated by the position of control knob 67. Barbs 64a and 64b are directed in their approach, respectively, to tissue surfaces 73 and 74.

It will be appreciated that the user may to an extent control the position and depth of the insertion of the respective anchors by moving the handle with respect to axis A, and through the rotation thereof about axis A. The depth of the insertion may to an extent be controlled through differential advancement of the suture placement device so as to advance one of the anchors more or less into the respective tissue surface. This extent of insertion into the space between the tissue surfaces and the depth of insertion will be within the control of the user and will depend upon the type of operation and the desired clinical outcome.

Figure 17:
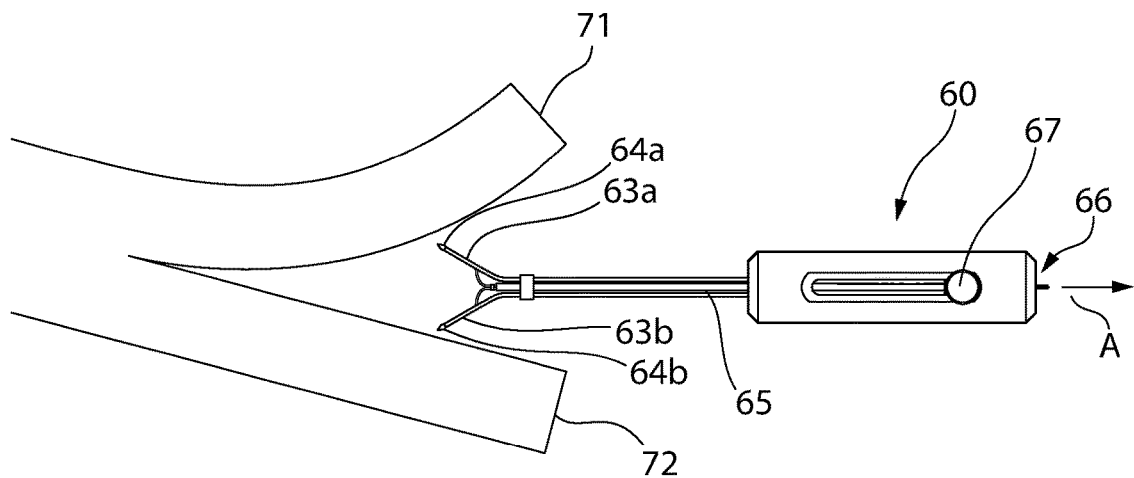
FIG. 17 is an isometric lateral view of the suture placement device in accordance with one embodiment of the present invention, shown in an approach to a representation of tissue to be joined.

FIG. 17 is an isometric lateral view of the suture placement device 60, showing a lateral view of an approach to a representation of tissue to be joined, and ready for insertion.

Figure 18:
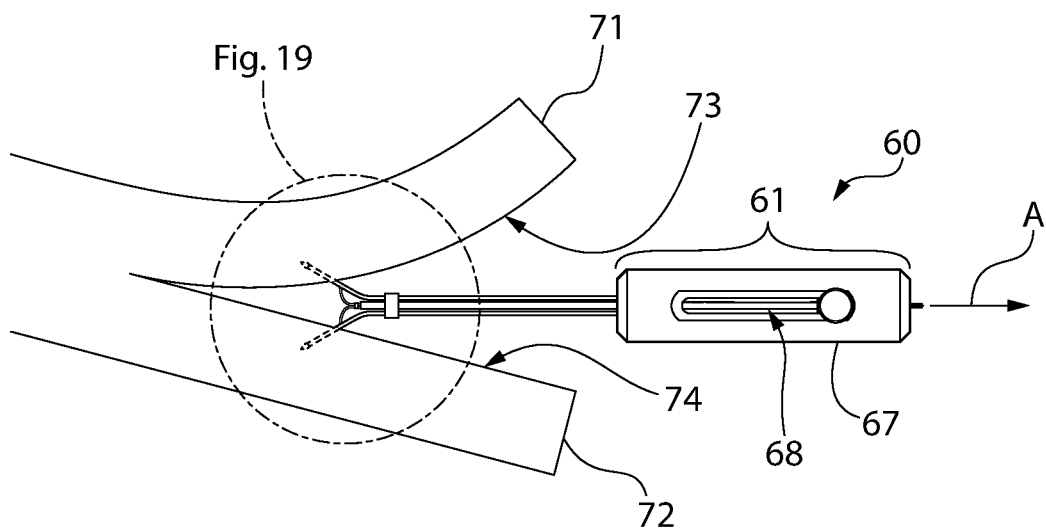
FIG. 18 is an isometric view of the suture placement device in accordance with one embodiment of the present invention, shown with the insertion portion directing barbed sutures into a representation of tissue to be joined.

FIG. 18 is an isometric view of the suture placement device 60, showing the insertion of barbs 64a and 64b by barb-directing portions 63a and 63b (see FIG. 12) into the tissue surfaces 73 and 74 requiring approximation (such as on either side of an incision, or the like).

Figure 19:
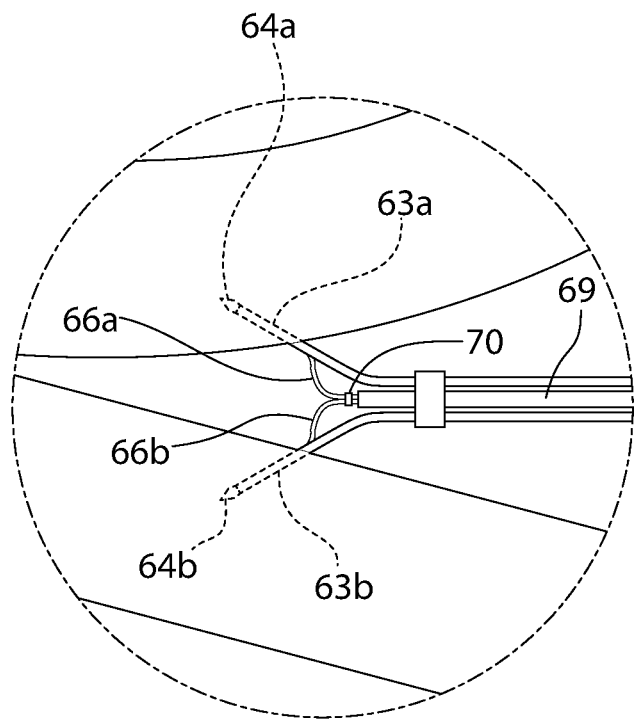
FIG. 19 is a detailed isometric lateral view of the insertion portion of a suture placement device in accordance with one embodiment of the present invention, shown with the insertion portion directing barbed sutures into a representation of tissue to be joined.

FIG. 19 is a detailed isometric lateral view of the insertion portion's barb-directing portions 63a and 63b of the suture placement device 60 as they guide insertion of barbs 64a and 64b into tissue surfaces 73 and 74.

Figure 20:
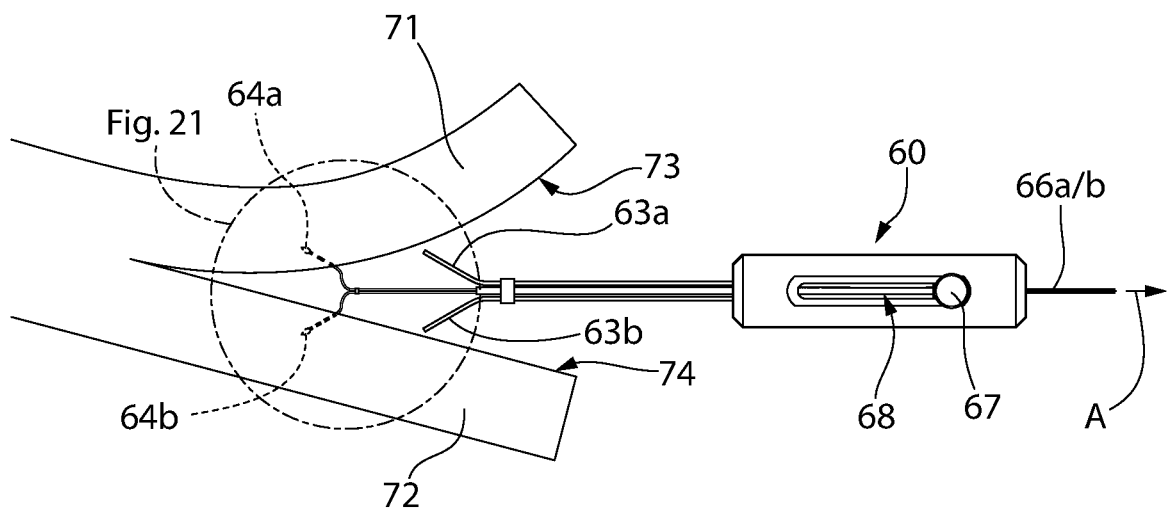
FIG. 20 is an isometric view of the suture placement device in accordance with one embodiment of the present invention, shown being withdrawn following insertion of barbed sutures into a representation of tissue to be joined.

FIG. 20 is an isometric view of the suture placement device 60, showing the barb-directing portions 63a and 63b directing barbed sutures having barbs 64a and 64b into a representation of tissue surfaces 73 and 74 to be approximated, and showing the suture placement device 60 withdrawn substantially along axis A to release barbs 64a and 64b from barb-directing portions 63a and 63b. In this view, the suture placement device 60 is withdrawn leaving the barb-tipped sutures 66a/64a and 66b/64b in the respective tissue surfaces 73 and 74.

Figure 21:
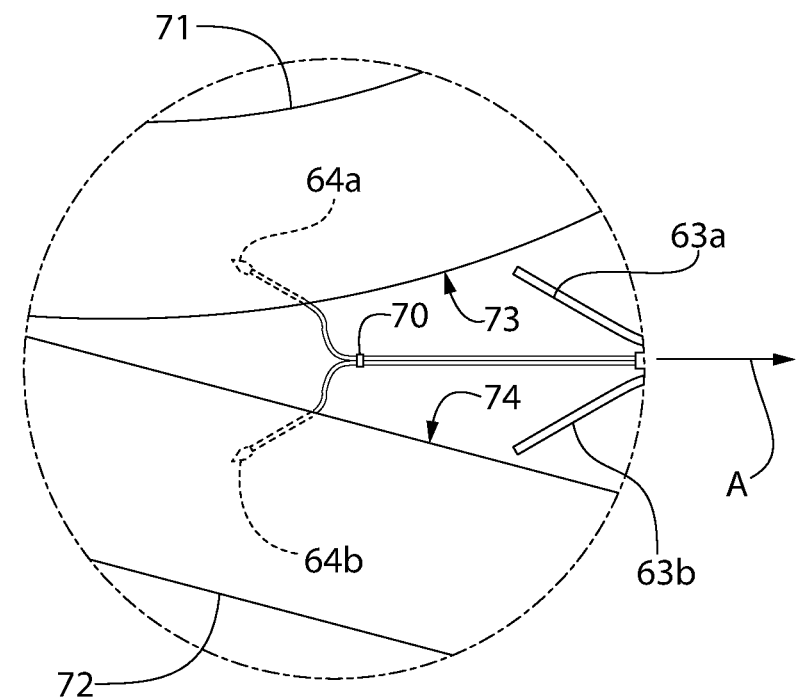
FIG. 21 is a detailed isometric lateral view of the insertion portion of a suture placement device in accordance with one embodiment of the present invention shown being withdrawn following insertion of barbed sutures into a representation of tissue to be joined.

FIG. 21 is a detailed isometric lateral view of the barb-directing portions 63a and 63b of a suture placement device 60 having released barbs 64a and 64b and being withdrawn substantially along axis A following insertion thereof into a representation of tissue surfaces 73 and 74.

Figure 22:
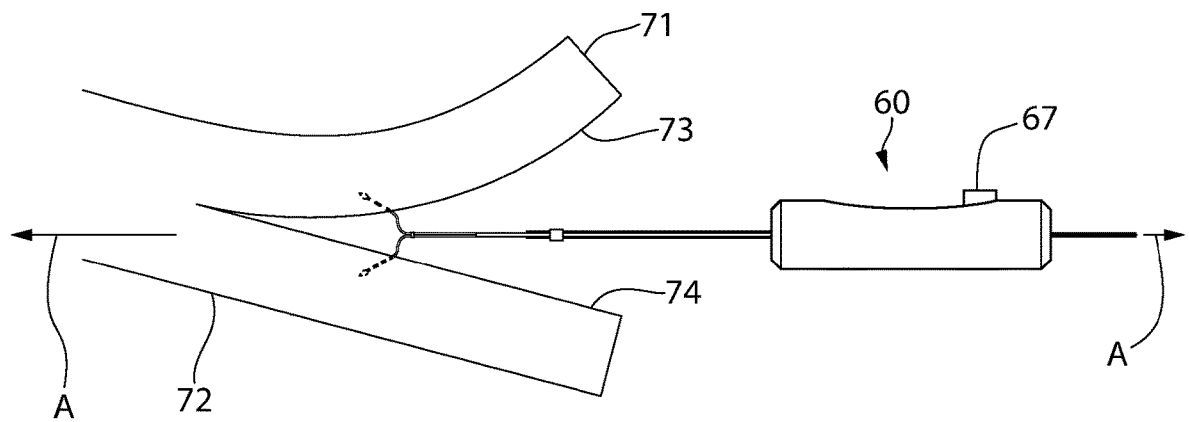
FIG. 22 is an isometric view of the suture placement device in accordance with one embodiment of the present invention, shown being rotated 90 degrees withdrawn following insertion of barbed sutures into a representation of tissue to be joined.

FIG. 22 is an isometric view of the suture placement device 60, shown being rotated about 90 degrees with respect to the plane containing the inserted barbs 64a and 64b (as indicated by the position of control knob 67) and with the hollow cinching cannula/suture conduit 65 still retracted to the rear position as indicated by the position of control knob 67, to best allow the tissue surfaces 73 and 74 to approximate.

Figure 23:
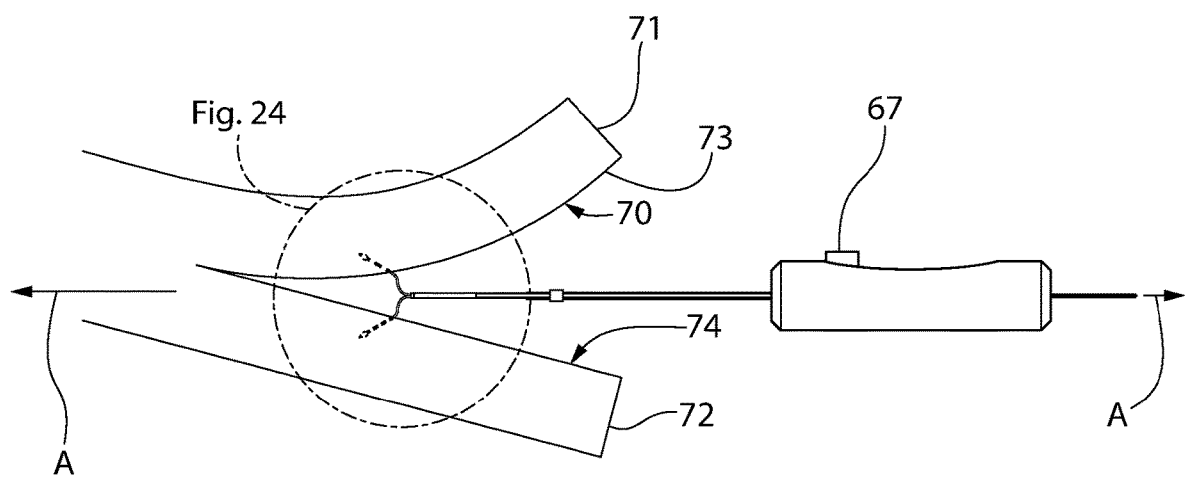
FIG. 23 is a detailed isometric lateral view of the insertion portion of a suture placement device in accordance with one embodiment of the present invention, shown being rotated 90 degrees withdrawn following insertion of barbed sutures into a representation of tissue to be joined and with the cinching cannula/suture conduit being extended.

FIG. 23 is an isometric view of the suture placement device 60, shown being rotated about 90 degrees with respect to the plane containing the inserted barbs 64a and 64b (see FIGS. 20 and 21), and with the hollow cinching cannula/suture conduit 65 advanced to the forward position to urge suture lock or cinching fixture 70 (see FIG. 21) distally so as to draw inserted barbs 64a and 64b toward one another and thereby approximate tissue surfaces 73 and 74 with the hollow cinching cannula/suture conduit 65 being extended from within outer cannula 69. In this way the barb-directing portions 63a and 63b of a suture placement device 60 do not interfere with the intended approximation of the tissue surfaces 73 and 74. The cinching cannula/suture conduit 65 may then be extended by manual action (such as through the use of control knob 67 or direct action upon the proximal end (i.e., opposite distal end 65a) of the hollow cannula/suture conduit 65b). Manual counterforce may also be applied directly to the proximal ends of barb-tipped suture lengths 66a and 66b. Thus, by holding the suture placement device 60 and the proximal ends of barb-tipped suture lengths 66a and 66b, the user can tension the distal ends of suture lengths 66a and 66b, drawing inserted barbs 64a and 64b toward one another and fixing them in place through cinching the suture lengths by action of cinching fixture 70.

Figure 24:
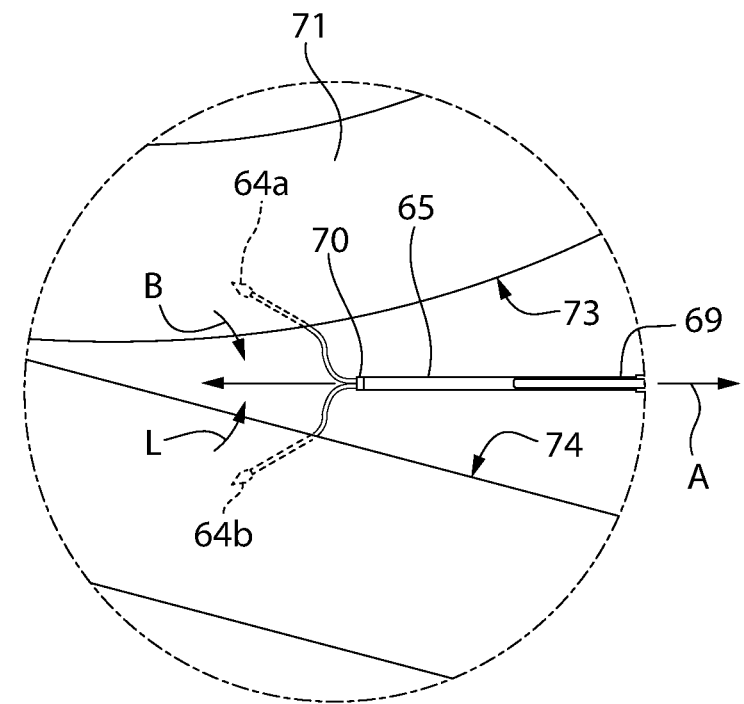
FIG. 24 is a detailed isometric view of the inserted barbed sutures into a representation of tissue to be joined and with the cinching cannula/suture conduit being extended.

FIG. 24 is a detailed isometric view of the inserted barbs 64a and 64b into a representation of tissue 71 and 72 to be joined and with the cinching hollow cannula/suture conduit 65 being extended to urge suture lock or cinching fixture 70 distally so as to draw inserted barbs 64a and 64b toward one another and thereby approximate tissue surfaces 73 and 74 substantially along lines B and C, with the hollow cinching cannula/suture conduit 65 being extended from within outer cannula 69.

Figure 25:
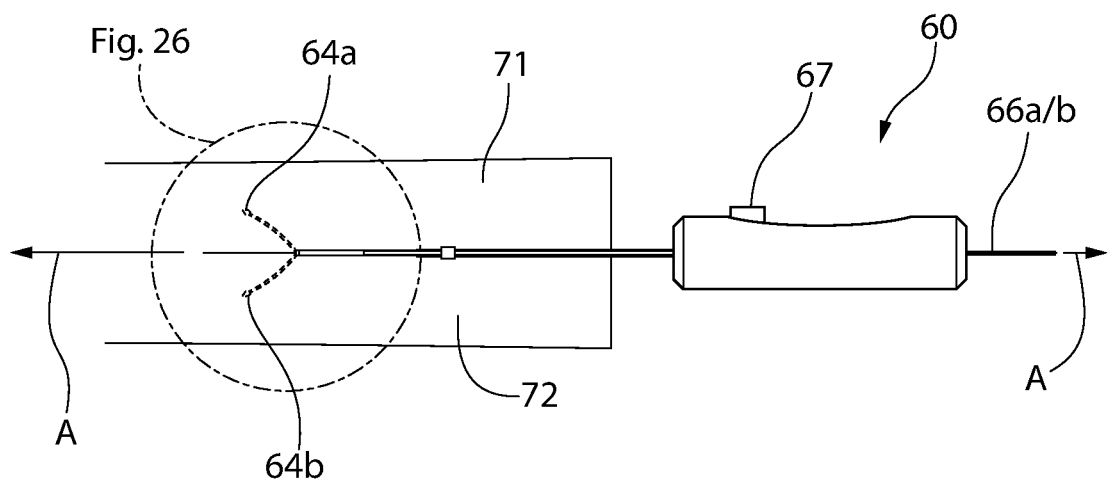
FIG. 25 is an isometric lateral view of the withdrawn suture placement device in accordance with one embodiment of the present invention, shown following closure of the represented tissue.

FIG. 25 is an isometric lateral view of the withdrawn suture placement device 60 following approximation of tissue surfaces 73 and 74 (see FIG. 24), and showing the extended suture material 66a and 66b.

In another variant, where a single suture (such as an angled, V-shaped suture or other multi-dentate suture forming an intersection of constituent anchor-bearing lengths is used) the distal portions of suture lengths 66a and 66b (and barbs 64a and 64b) are essentially replaced by a separate suture length that extends through the hollow cinching cannula/suture conduit 65 and loops around the angled suture (or other multi-dentate suture) intersection to permit the user to exert counterforce as the hollow cinching cannula/suture conduit 65 is urged forward against suture lock or cinching fixture 70 as described herein.

Figure 26:
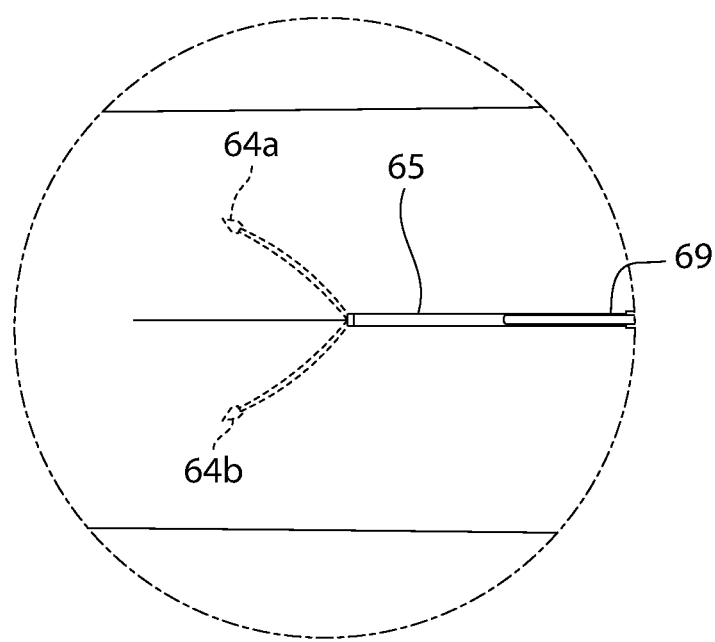
FIG. 26 is a detailed isometric lateral view of the cinching cannula/suture conduit being extended and shown following closure of the represented tissue by the barbed suture, in accordance with one embodiment of the present invention.

FIG. 26 is a detailed isometric lateral view of hollow cinching cannula/suture conduit 65 being extended from within outer cannula 69 and shown following closure of the represented tissue surfaces 73 and 74 (see FIG. 24) by the barbed suture held by inserted barbs 64a and 64b.

Figure 27:
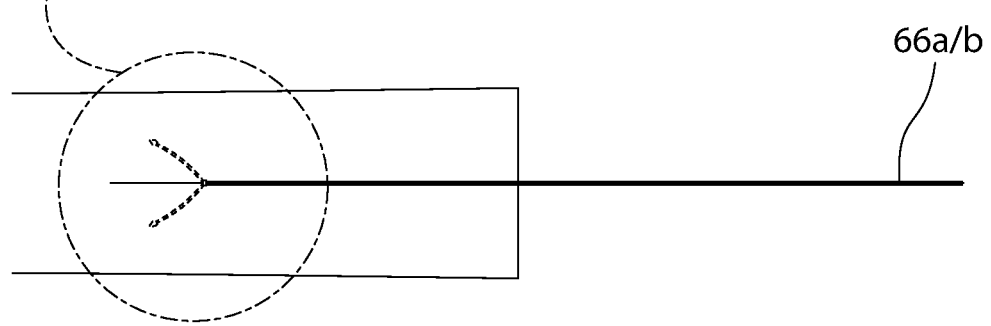
FIG. 27 is an isometric lateral view of the closure of the represented tissue by the barbed suture, following withdrawal of the suture placement device, in accordance with one embodiment of the present invention.

FIG. 27 is an isometric lateral view of the closure of the represented tissue by the barbed suture, following withdrawal of the suture placement device 60 along axis A. The user thus may release the proximal ends of suture material 66a and 66b, withdraw the suture placement device from around the suture material, and allow the suture material to be trimmed as desired.

Figure 28:
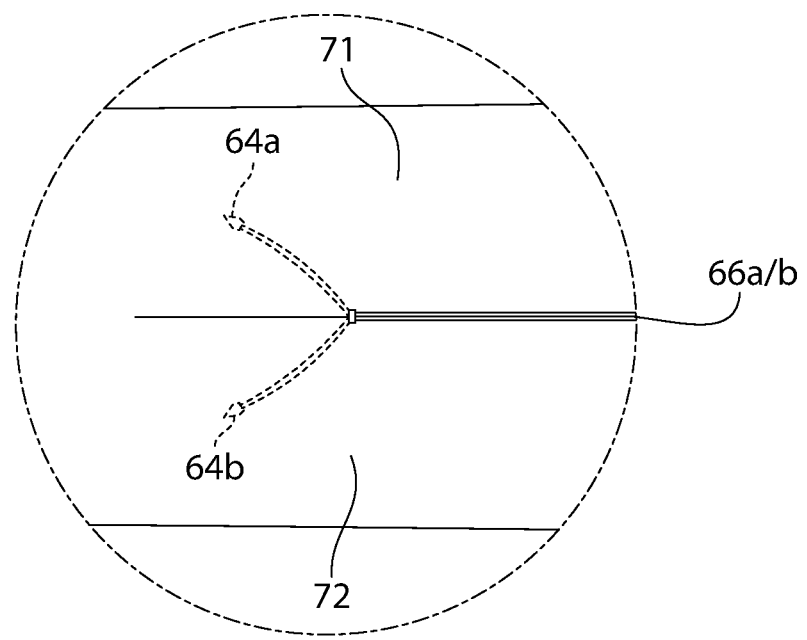
FIG. 28 is a detailed isometric lateral view of the closure of the represented tissue by the barbed suture, following withdrawal of the suture placement device, in accordance with one embodiment of the present invention.

FIG. 28 is a detailed isometric lateral view of the closure of the represented tissue surfaces 73 and 74 (see FIG. 24) by the barbed suture, following withdrawal of the suture placement device 60, leaving extended suture material 66a and 66b.

Figure 29:
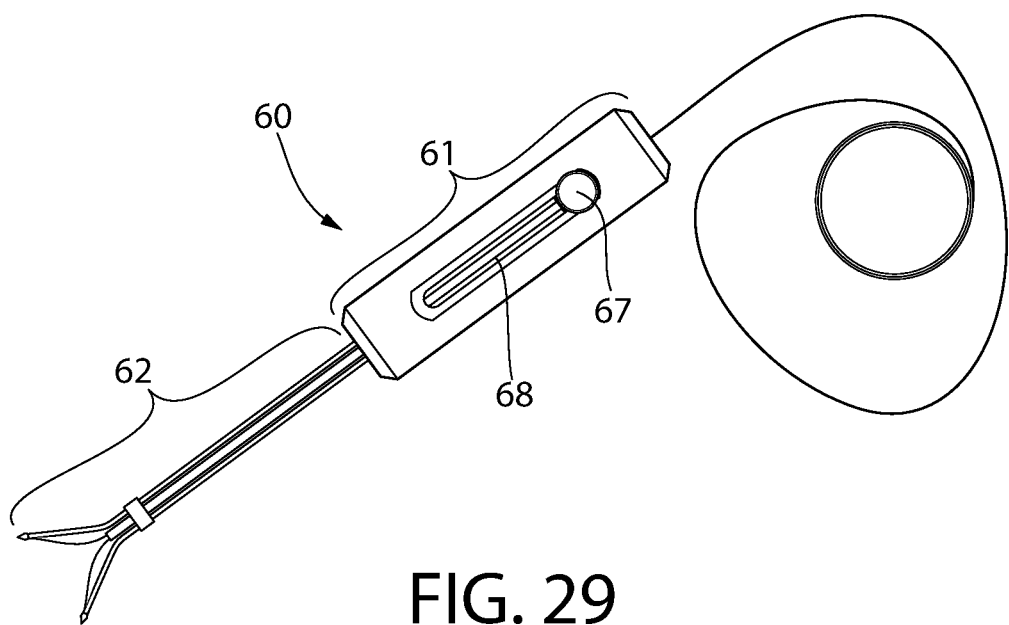
FIG. 29 is a photographic perspective view of a suture placement device in accordance with one embodiment of the present invention with the cinching cannula/suture conduit being retracted.

FIG. 29 is a photographic perspective view of a suture placement device 60 in accordance with one embodiment of the present invention with the hollow cinching cannula/suture conduit 65 being retracted.

Figure 30:
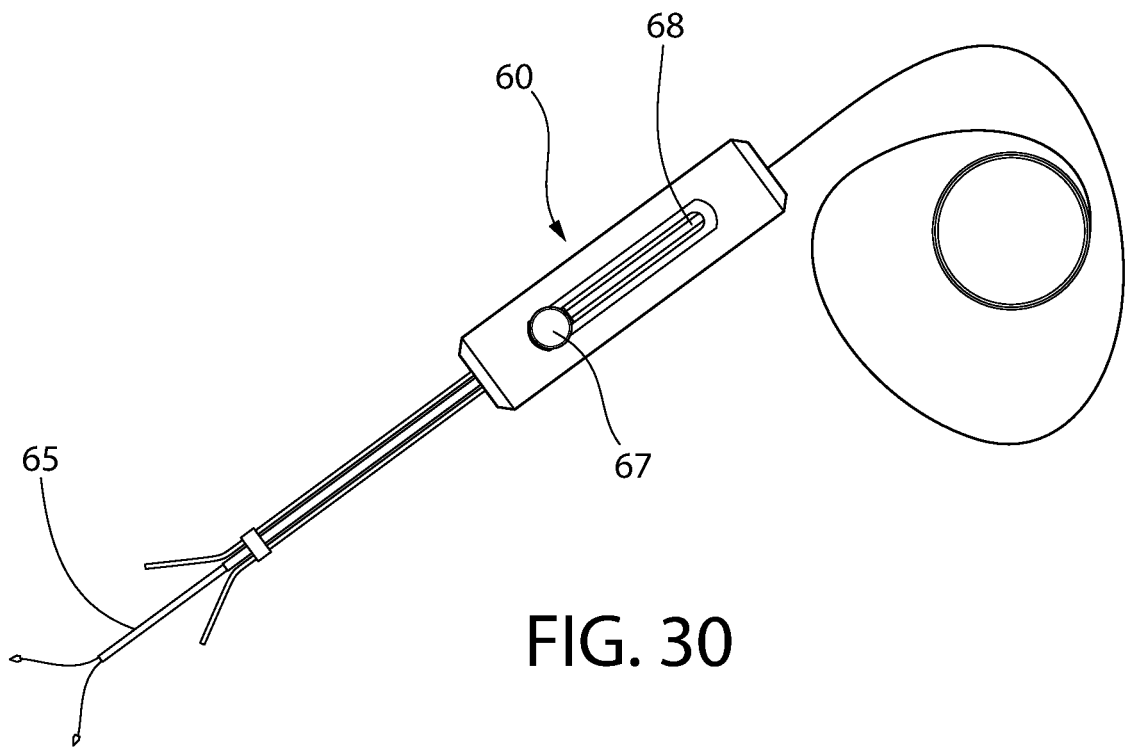
FIG. 30 is a photographic perspective view of a suture placement device in accordance with one embodiment of the present invention with the cinching cannula/suture conduit being extended.

FIG. 30 is a photographic perspective view of a suture placement device in accordance with one embodiment of the present invention with the hollow cinching cannula/suture conduit 65 being extended.

Figure 31:
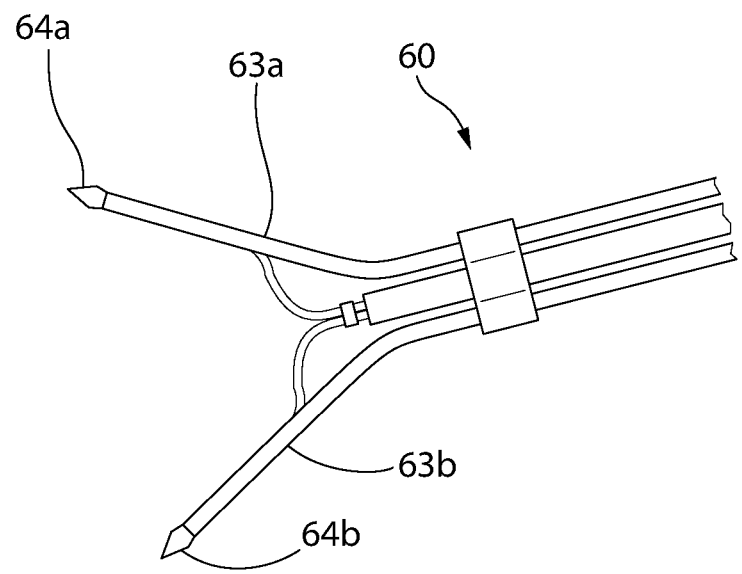
FIG. 31 is a detailed photographic perspective view of the insertion portion of a suture placement device in accordance with one embodiment of the present invention with the cinching cannula/suture conduit being extended.

FIG. 31 is a detailed photographic perspective view of the barb-directing portions 63a and 63b of a suture placement device 60 in accordance with one embodiment of the present invention with the hollow cinching cannula/suture conduit 65 being retracted.

The foregoing is but one embodiment of the invention.

It will be appreciated that other variations using more than two anchor-insertion arms, such as a tri-dentate quadra-dentate variations, for application where it is desired to place multiple anchors simultaneously. Such devices may be constructed by adding additional anchor-directing portions (such as 63a and 63b) about the path of the hollow cinching cannula/suture conduit, and such additional anchor-directing portions may be of the same or varied lengths and at any angle to one another so as to orient the anchor-directing portions spatially depending upon the desired application by presenting the anchor-directing portions at any orientation in space.

In such multi-dentate devices, it will be understood that the anchor insertion portion typically will be fully withdrawn from the approximation area to eliminate any interference with the approximation by the structure of the multi-dentate distal end, as such multi-dentate distal ends may not as easily be rotated out of the way to permit approximation of facing tissues, as is possible in the case of the angled (such as multi-V-shaped) device.

It will also be appreciated that the devices may be varied with respect to the lengths of the constituent anchor-insertion arms, and/or the angles of the anchor-insertion arms with respect to one another, such that the spatial array of the anchor-insertion points may be tailored to specific tissues, tissue types or tissue surfaces and/or tissue presentments requiring approximation, or differing tissue approximation environments, such as those presented in mastectomies or in tumor resection.

Other variations and embodiments of the invention include those devices and methods that may be adapted for laparoscopic surgery or other types of minimally invasive surgery. Such device variants include those wherein the above-described handle portion may be eliminated in favor of using a simple hand-actuated hollow cinching cannula/suture conduit so as to reduce the width of the device to best accommodate laparoscopic surgery or keyhole surgery. In this embodiment, the hollow cinching cannula/suture conduit may be thumb actuated by the user, or may be fitted with a thumb wheel to allow the user to advance the hollow cinching cannula/suture conduit with respect to the anchor-directing portions, to cinch the suture lengths while counterforce is exerted and maintained, as otherwise described herein for manual operation involving use of the handle portion.

In similar fashion, other variations and embodiments of the invention include those devices and methods that may be adapted for robotic surgery. In this variant, the handle portion may be eliminated in favor of a fitment to affix the device to a robotic arm that permits the anchor-directing portions, such as barb-directing portions 63a and 63b, robotically to be advanced (and where required rotated) and the hollow cinching cannula/suture conduit robotically to be actuated to cinch the suture lengths while counterforce is exerted and maintained, as described herein for manual operation.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A suture article adapted to be inserted into opposing tissue surfaces at two respective locations and to draw said tissue surfaces toward one another, said suture article comprising:
   a. at least two lengths of suture material, each said length having a terminal distal end having a tissue anchor of a bioresorbable polymeric material and having a terminal distal barb point directed distally from said terminal distal and adapted to pierce a tissue surface and said tissue anchor adapted to resist withdrawal from respective said opposing tissue surfaces, and an opposite proximal end, said lengths being arranged alongside one another such that said terminal distal ends are collateral; and b. a cinching fixture adapted to slidingly engage said lengths so as to be able to move from said opposite proximal ends toward said terminal distal ends, so as to move said tissue anchors from a relatively more distant position to a relatively near position with respect to one another, and so as to maintain said tissue anchors in said relatively near position;

each of said at least two lengths of suture material having respective sub lengths, and said cinching fixture defining an independent suture material path for each of said sub-lengths, and wherein said suture material path is linear.

2. A suture article according to claim 1 wherein said cinching fixture is of a relatively rigid material and comprises relatively flexible frictional extensions extending into each of said suture material paths.

3. A suture article according to claim 1 additionally comprising a third length of suture material, said third length having a terminal distal end having an anchor of a bioresorbable polymeric material and having a terminal distal barb point directed distally from said terminal distal and adapted to pierce a third tissue surface and said third anchor adapted to resist withdrawal from a respective third tissue surface, and an opposite proximal end, said lengths being arranged alongside one another such that said terminal distal ends are collateral.

4. A suture placement device adapted to insert into a tissue surface, said device comprising:
   a. a handle portion having an insertion-directed end;
   b. a first insertion portion extending from said insertion-directed end of said handle portion and comprising a proximal end and a first distal end, said first distal end comprising a first anchor-directing portion, said first anchor-directing portion being releasably engaged to a first tissue anchor of a bioresorbable polymeric material by said first tissue anchor having (i) a first portion releasably inserted into said first anchor-directing portion and (ii) a second portion extending from said first anchor-directing portion and having a terminal distally directed point adapted to pierce a tissue surface and said first tissue anchor adapted to resist withdrawal from said tissue surface, said first tissue anchor having a first terminal end and said first anchor-directing portion directing said first terminal distal point distally of said first distal end of said first insertion portion, wherein said first tissue anchor comprises a first suture that extends through the length of the first insertion portion; and c. a second insertion portion extending from said insertion-directed end of said handle portion and comprising a proximal end and a second distal end, said second distal end comprising a second anchor-directing portion, said second anchor-directing portion being releasably engaged to a second tissue anchor of a bioresorbable polymeric material by said second tissue anchor having (i) a first portion releasably inserted into said second anchor-directing portion, and (ii) a second portion extending from said second anchor-directing portion and having a terminal distally directed point adapted to pierce a tissue surface and said second tissue anchor adapted to resist withdrawal from said tissue surface, said tissue anchor having a second terminal end and said second anchor-directing portion directing said second terminal distal point distally of said second distal end of said second insertion portion, wherein said second tissue anchor comprises a second suture that extends through the length of the second insertion portion.

5. A suture placement device according to claim 4 additionally comprising a cinching fixture adapted to slidingly engage said lengths of suture material so as to be able to move from said opposite end toward said terminal distal end and to resist movement once positioned along said lengths of suture material.

6. A suture placement device according to claim 4 wherein said first insertion portion and second insertion portion are disposed at an angle.

* * * * *